US011337850B1

(12) United States Patent
Ward et al.

(10) Patent No.: US 11,337,850 B1
(45) Date of Patent: May 24, 2022

(54) FLUID DELIVERY LINE AND CONNECTION SYSTEM FOR TARGETED TEMPERATURE MANAGEMENT SYSTEM

(71) Applicant: C. R. Bard, Inc., Franklin Lakes, NJ (US)

(72) Inventors: Alistair J. Ward, Stretham (GB); Dall G. Amos, Sawston (GB); Carl G. Hewett, St. Neots (GB); Andrew R. Taylor, Cambridge (GB); Harry D. Turner, Cambridge (GB); Leanne Y. Win, Cambridge (GB); Trevor Beckett, Cambridge (GB)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/313,771

(22) Filed: May 6, 2021

(51) Int. Cl.
*A61F 7/00* (2006.01)
*A61F 7/02* (2006.01)

(52) U.S. Cl.
CPC .............. *A61F 7/00* (2013.01); *A61F 7/0085* (2013.01); *A61F 7/02* (2013.01); *A61F 2007/0054* (2013.01)

(58) Field of Classification Search
CPC .............................................. A61F 2007/0054
See application file for complete search history.

(56) References Cited

U.S. PATENT DOCUMENTS

| | | | |
|---|---|---|---|
| 5,897,142 A | 4/1999 | Kulevsky | |
| 7,434,842 B2 | 10/2008 | Schmidt | |
| 8,221,389 B2 | 7/2012 | Brenner et al. | |
| 8,622,980 B2 | 1/2014 | Zinn | |
| 8,683,996 B2 | 4/2014 | Allen et al. | |
| 9,283,109 B2 | 3/2016 | Guyuron et al. | |
| 10,471,247 B2 | 11/2019 | Kellner et al. | |
| 10,632,321 B2 * | 4/2020 | Schwarz | A61N 2/02 |
| 10,677,688 B2 | 6/2020 | Rivas et al. | |
| 2011/0152982 A1 * | 6/2011 | Richardson | A61F 7/02 607/104 |
| 2013/0138185 A1 | 5/2013 | Paxman et al. | |
| 2014/0046411 A1 | 2/2014 | Elkins et al. | |
| 2018/0042762 A1 | 2/2018 | Galer | |
| 2018/0163907 A1 | 6/2018 | Brugger et al. | |

(Continued)

FOREIGN PATENT DOCUMENTS

EP          2471574 A1     7/2012

*Primary Examiner* — Kaitlyn E Smith
(74) *Attorney, Agent, or Firm* — Rutan & Tucker LLP

(57) ABSTRACT

A fluid delivery line (FDL) for use in transporting a targeted temperature management (TTM) fluid between a TTM module and a thermal contact pad is disclosed. The FDL can include a bi-luminal fluid conduit and a bi-luminal proximal FDL connector. The two lumens of the proximal connector can be concentrically arranged. An authentication tag attached to the FDL can provide authentication data to a TTM module. A TTM system can include a connection adapter added to an existing TTM module where the adapter includes the electro-mechanical valves. An adapter controller operates the valves in accordance with obtained authentication data from the tag. Fluid connection systems can include valves that automatically open and close upon connection and disconnection. Fluid conduits and connectors can include concentrically arranged fluid lumens.

29 Claims, 20 Drawing Sheets

(56) References Cited

U.S. PATENT DOCUMENTS

| | | |
|---|---|---|
| 2019/0192337 A1 | 6/2019 | Taylor et al. |
| 2020/0282197 A1 | 9/2020 | Langer et al. |
| 2020/0289361 A1 | 9/2020 | Tian et al. |

\* cited by examiner

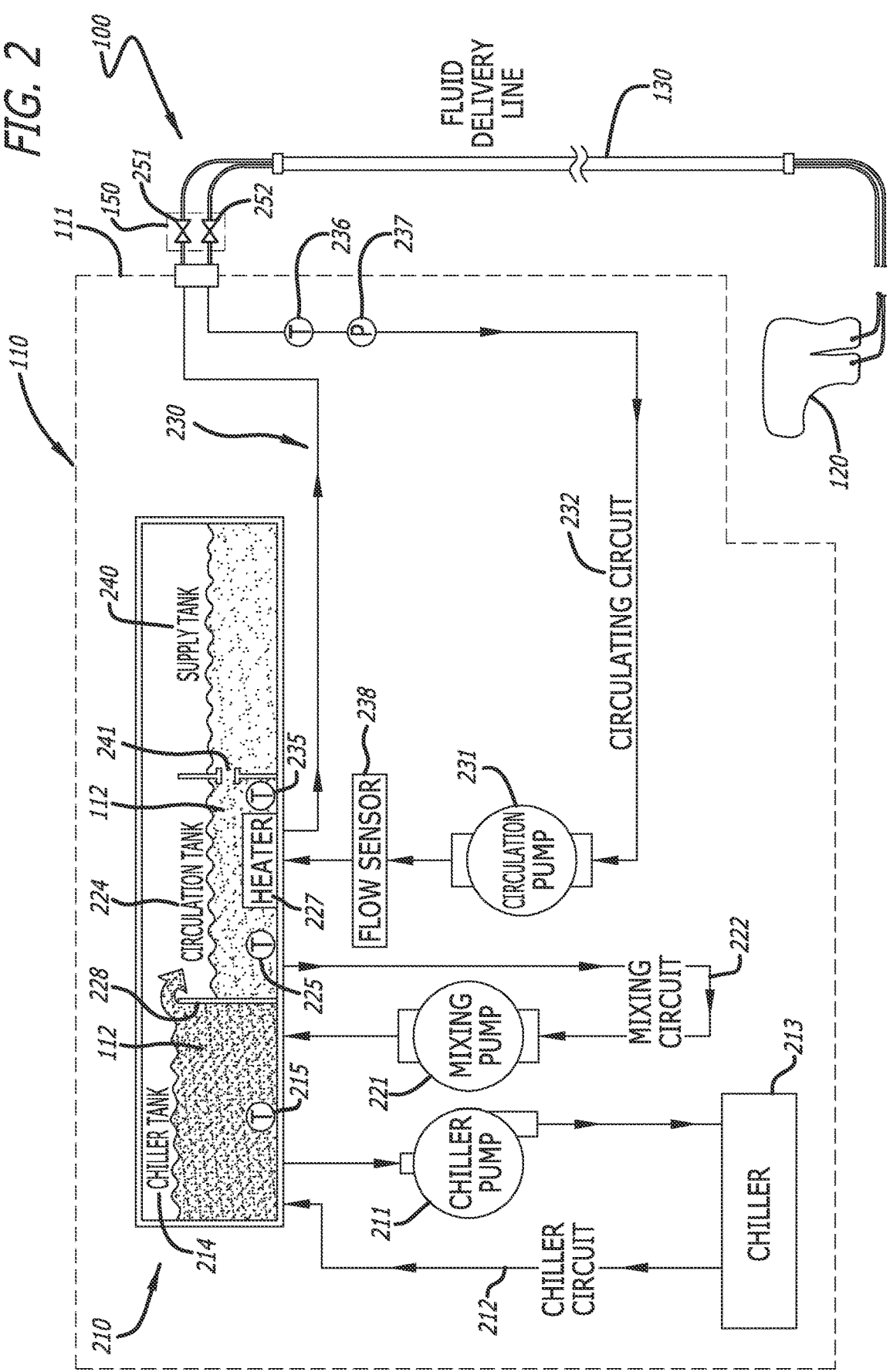

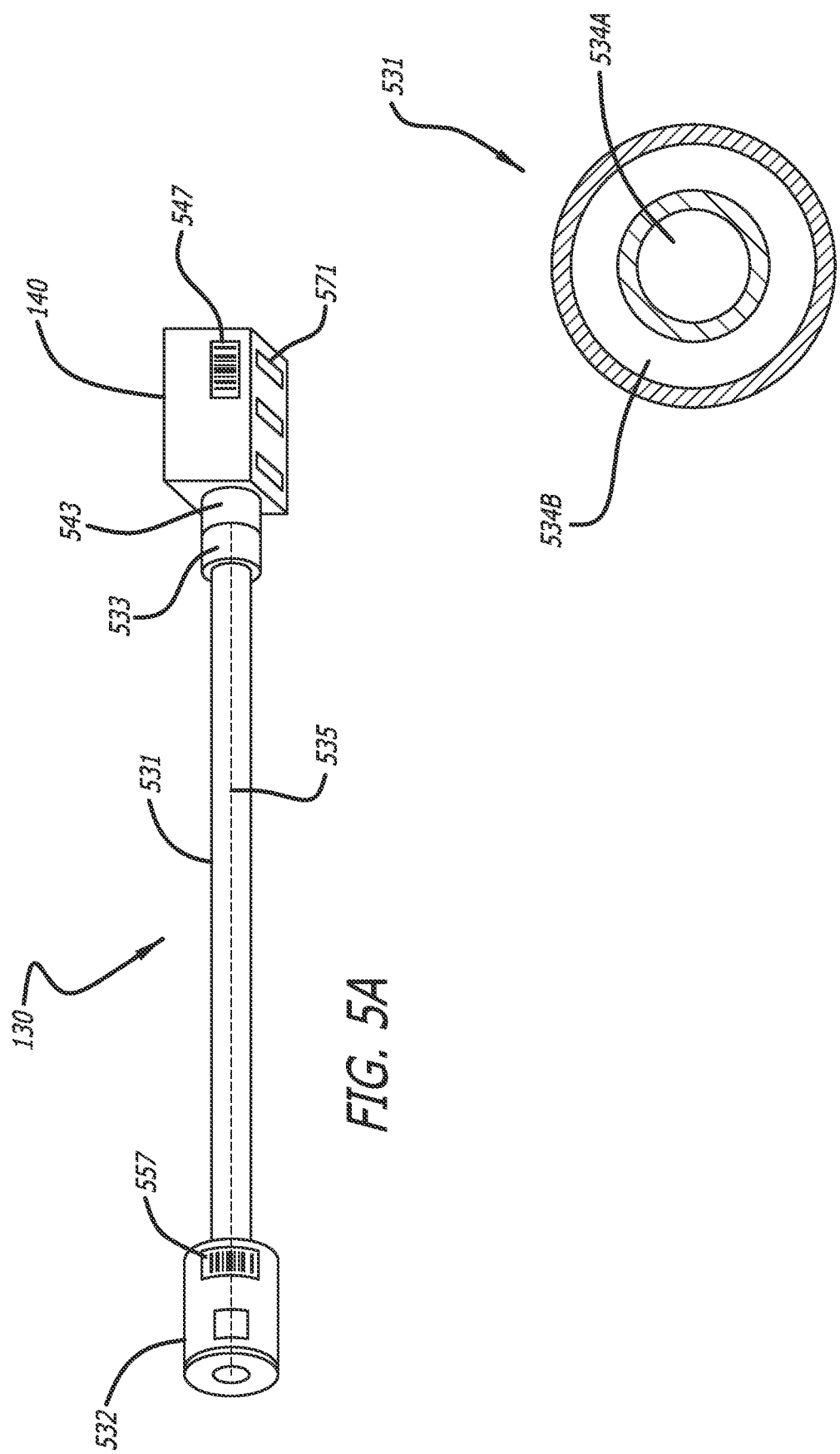

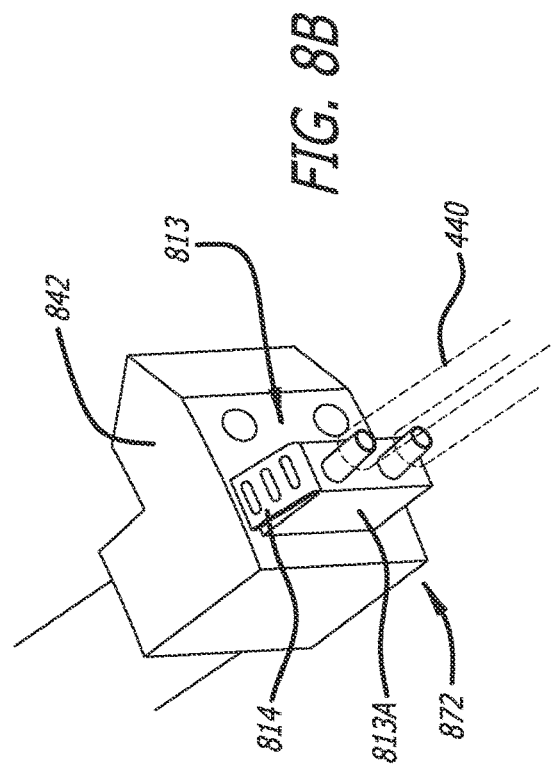
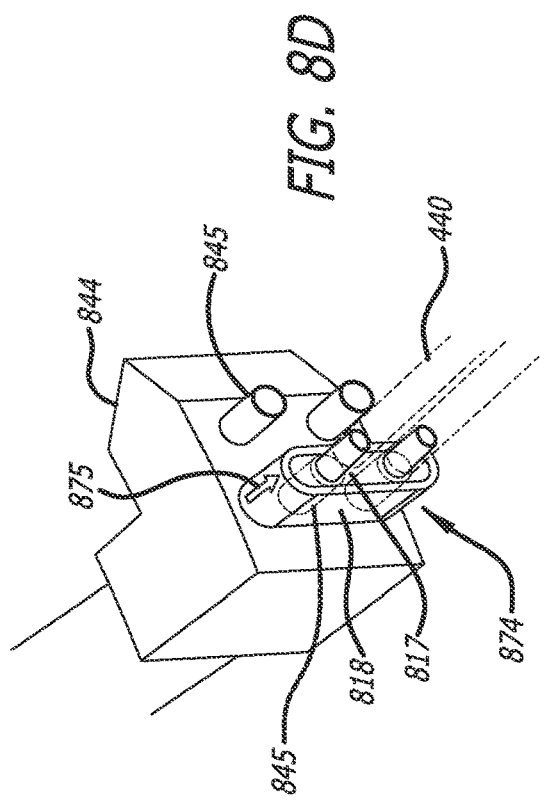
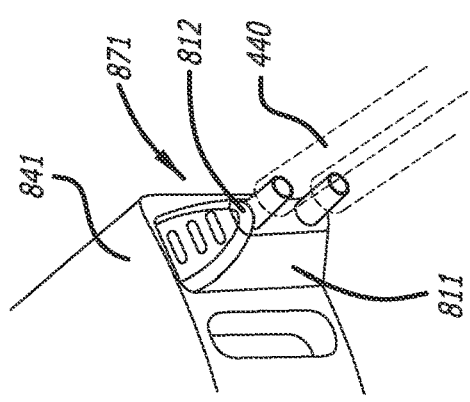
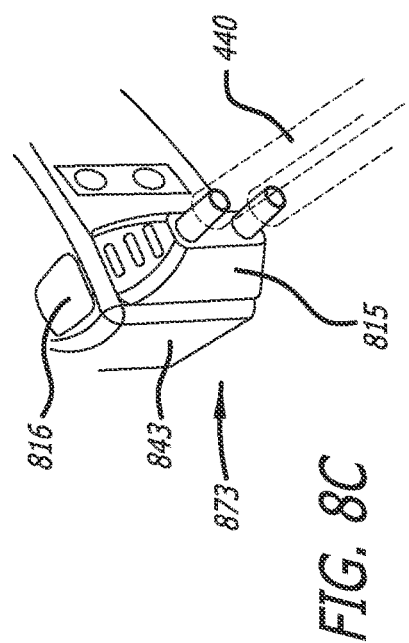

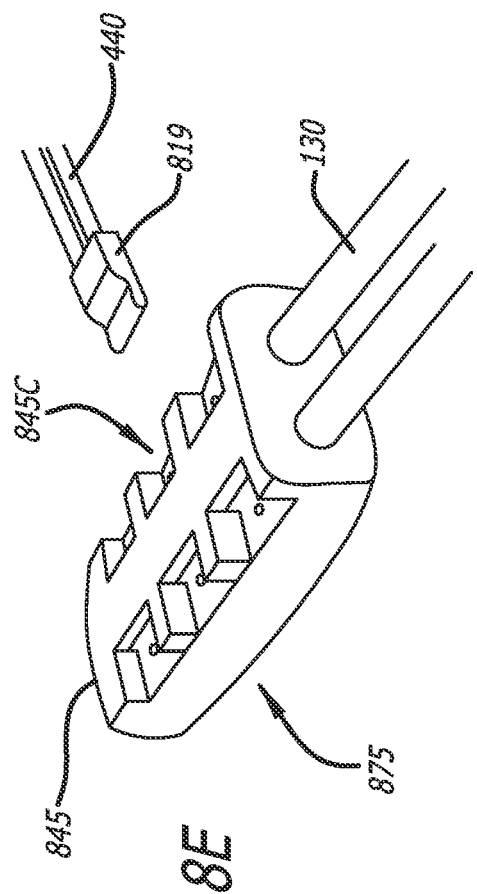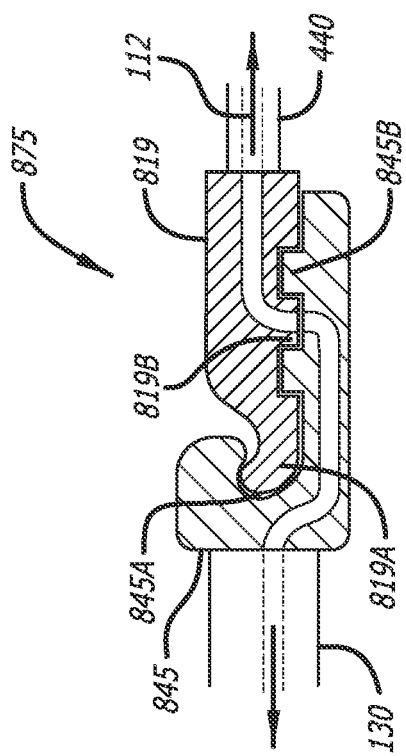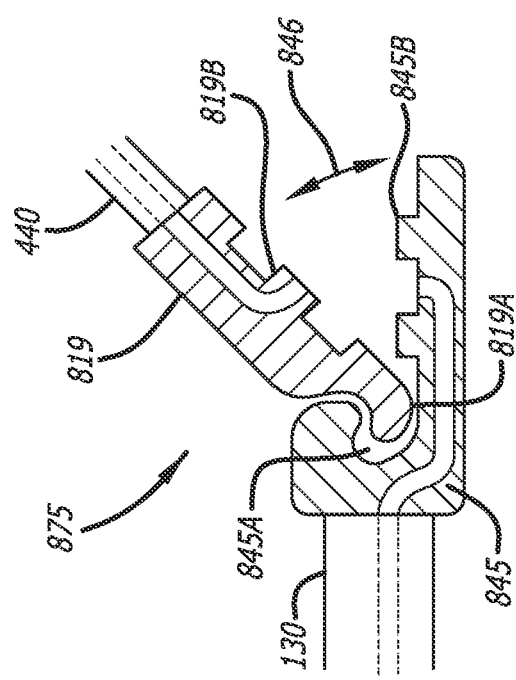

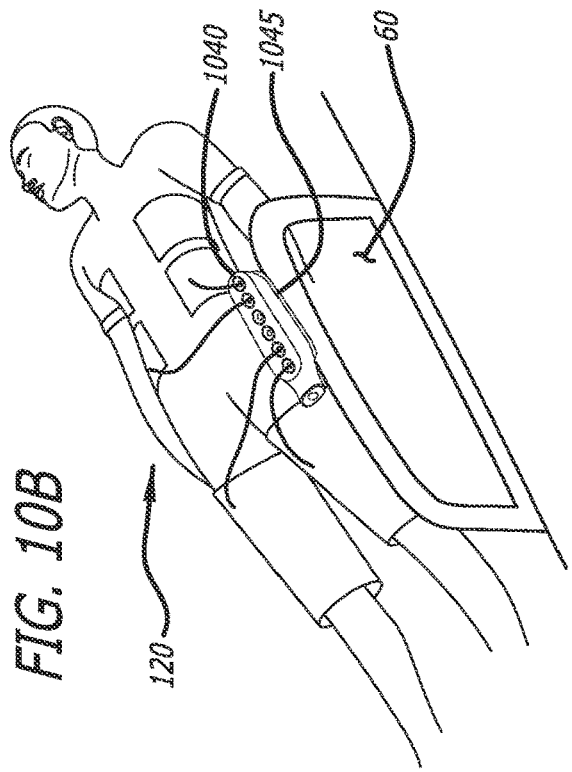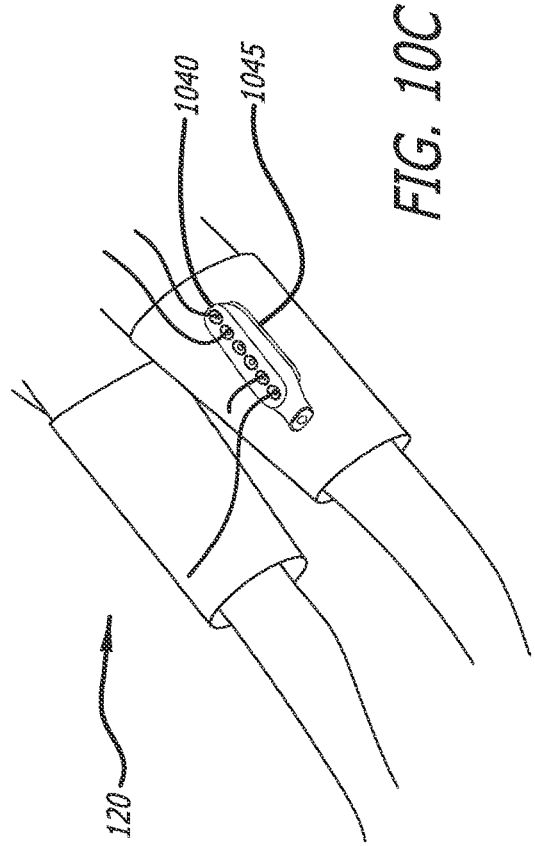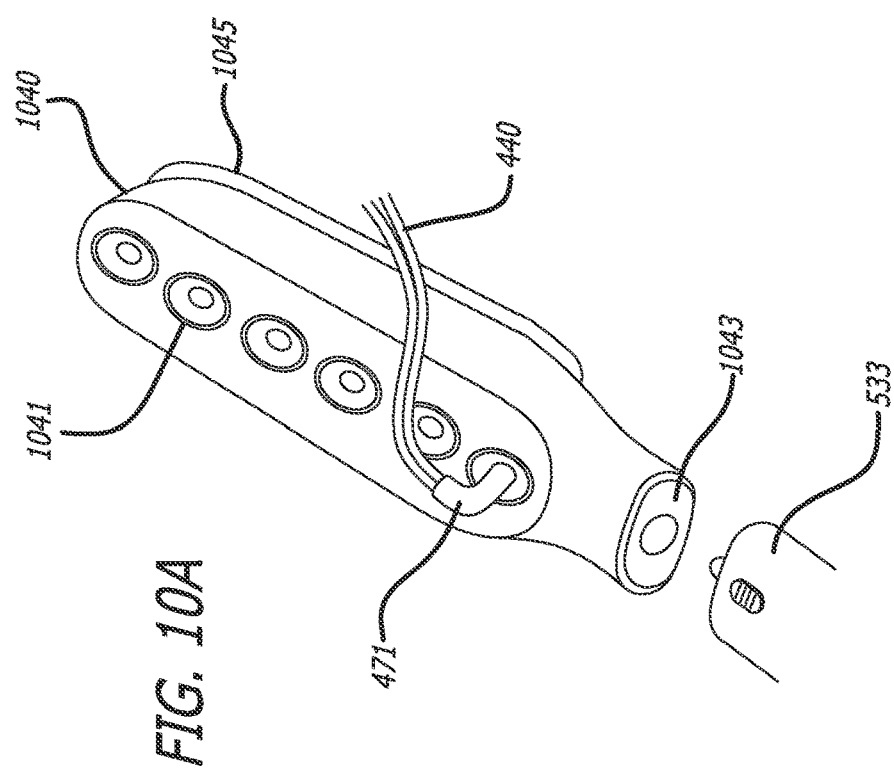

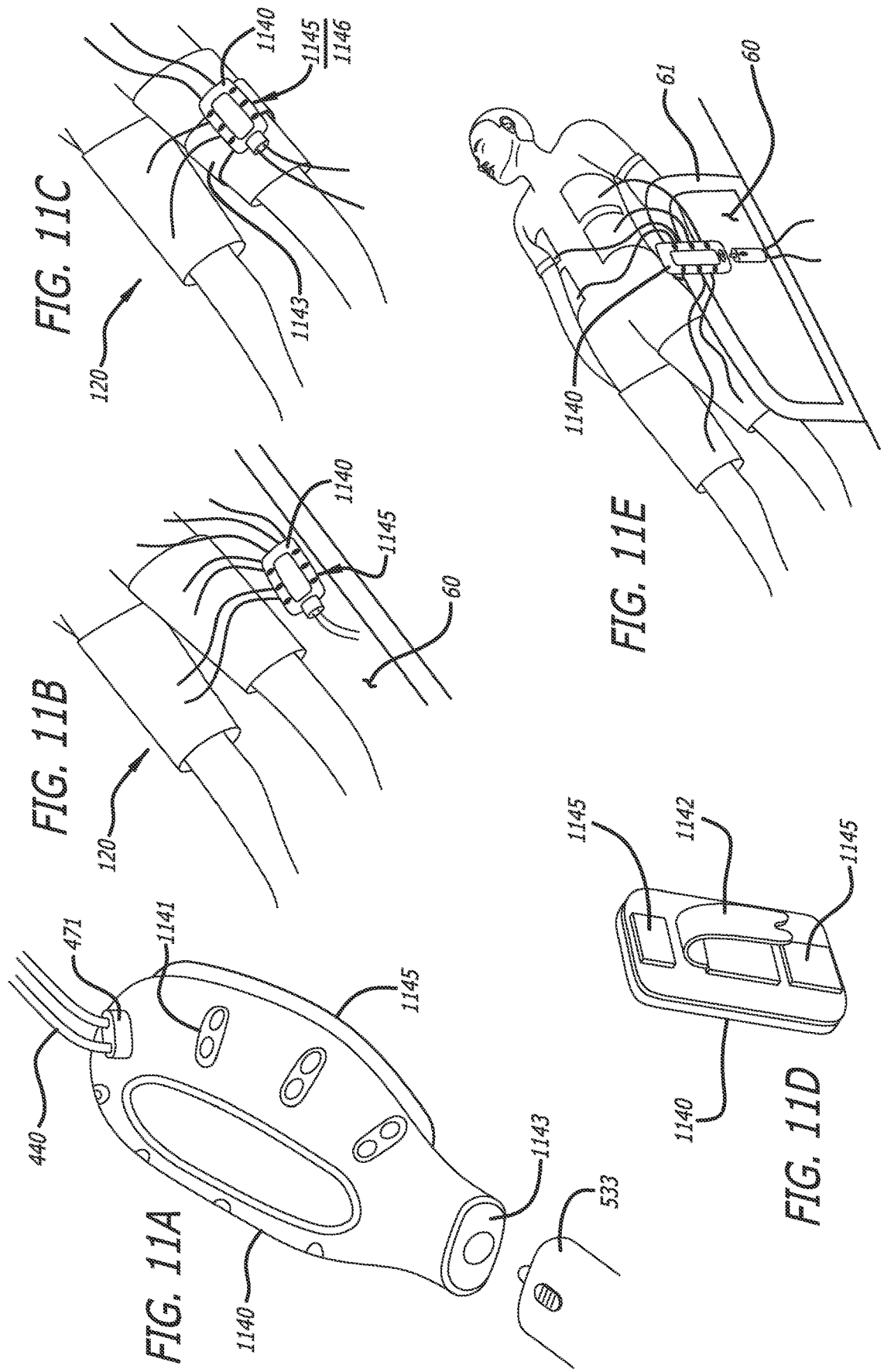

FLUID DELIVERY LINE AND CONNECTION SYSTEM FOR TARGETED TEMPERATURE MANAGEMENT SYSTEM

BACKGROUND

The effect of temperature on the human body has been well documented and the use of targeted temperature management (TTM) systems for selectively cooling and/or heating bodily tissue is known. Elevated temperatures, or hyperthermia, may be harmful to the brain under normal conditions, and even more importantly, during periods of physical stress, such as illness or surgery. Conversely, lower body temperatures, or mild hypothermia, may offer some degree of neuroprotection. Moderate to severe hypothermia tends to be more detrimental to the body, particularly the cardiovascular system.

Targeted temperature management can be viewed in two different aspects. The first aspect of temperature management includes treating abnormal body temperatures, i.e., cooling the body under conditions of hyperthermia or warming the body under conditions of hypothermia. The second aspect of thermoregulation is an evolving treatment that employs techniques that physically control a patient's temperature to provide a physiological benefit, such as cooling a stroke patient to gain some degree of neuroprotection. By way of example, TTM systems may be utilized in early stroke therapy to reduce neurological damage incurred by stroke and head trauma patients. Additional applications include selective patient heating/cooling during surgical procedures such as cardiopulmonary bypass operations.

TTM systems circulate a fluid (e.g., water) through one or more thermal contact pads coupled with a patient to affect surface-to-surface thermal energy exchange with the patient. In general, TTM systems include a TTM fluid control module coupled with a thermal contact pad set via a fluid deliver line. One such TTM system is disclosed in U.S. Pat. No. 6,645,232, titled "Patient Temperature Control System with Fluid Pressure Maintenance" filed Oct. 11, 2001 and one such thermal contact pad and related system is disclosed in U.S. Pat. No. 6,197,045 titled "Cooling/heating Pad and System" filed Jan. 4, 1999, both of which are incorporated herein by reference in their entireties. The fluid delivery line generally includes two fluid conduits for transporting TTM fluid to and from the thermal pad set. The thermal pads may include connectors to facilitate connection to and disconnection from the fluid delivery line.

SUMMARY OF THE INVENTION

Embodiments herein generally relate to the selective raising and/or lowering of patient temperatures, and in particular embodiments, to systems and methods for controlling a patient's temperature via the circulation of heated/cooled fluid through one or more pads contacting a patient.

Briefly summarized, disclosed herein is a fluid delivery line (FDL) for use in transporting a targeted temperature management (TTM) fluid between a TTM module and a thermal contact pad applied to a patient. The FDL includes a bi-luminal fluid conduit extending from a proximal end to a distal end and a bi-luminal proximal FDL connector at the proximal end. The proximal FDL connector is configured to couple with the TTM module, and the two lumens of the proximal connector are concentrically arranged. A bi-luminal distal connector at the distal end is configured to couple with a manifold hub. The distal connector includes a pair of valves, where each valve is disposed in line with a separate one of the two lumens. Each valve is configured to automatically prevent fluid flow through its respective lumen upon decoupling of the distal connector from the hub, and each valve is configured to automatically allow/permit fluid flow through its respective lumen upon coupling of the distal connector with the hub.

The distal connector may include a latching mechanism having a displaceable member, such that when the displaceable member is in a displaced state, detachment of the distal connector from the hub is allowed, and when the displaceable member is in a non-displaced state, detachment of the distal connector from the hub is prevented. The two lumens of the distal connector may be concentrically arranged.

In some embodiments, coupling the proximal FDL connector with TTM module includes connecting the proximal FDL connector to a module connector of the TTM module, and pivoting the proximal FDL connector such that a longitudinal axis of the proximal FDL connector is pivoted from a substantially horizontal orientation to a substantially vertical orientation (or vice versa).

The proximal FDL connector may be configured to latch to the TTM module, such that when the proximal FDL connector is oriented horizontally, the latching mechanism is deactivated and separation of the proximal FDL connector from the adapter is allowed, and when the proximal FDL connector is oriented vertically, the latching mechanism is activated and separation of the proximal FDL connector from the adapter is prevented. It should be noted that horizontal and vertical orientations may be reversed in alternative embodiments.

The proximal FDL connector may include a pair of proximal valves, each proximal valve is disposed in line with a separate one of the two lumens of the proximal FDL connector, where each proximal valve is configured to automatically prevent fluid flow through its respective lumen upon decoupling of the proximal FDL connector from the TTM module, and each proximal valve is configured to automatically allow fluid flow through its respective lumen upon coupling of the proximal FDL connector with the TTM module.

In some embodiments, the FDL includes an authentication tag configured to provide FDL authentication data to the TTM module.

In some embodiments, the FDL is coupled with the manifold hub, where the hub includes a plurality of bi-luminal distal hub connectors configured to the couple with a plurality of thermal contact pads. In other embodiments, the FDL is coupled with more than one manifold hub, where each manifold hub includes a plurality of bi-luminal distal hub connectors configured to the couple with a plurality of thermal contact pads.

In some embodiments, the two lumens of the fluid conduit are concentrically arranged along at least a portion of the fluid conduit.

Also disclosed herein is a thermal contact pad assembly for exchanging thermal energy between a targeted temperature management (TTM) fluid a patient. The assembly includes a thermal contact pad and a manifold hub. The pad includes a pad portion configured for placement on the patient, a bi-luminal fluid conduit extending proximally away from the pad portion, and a bi-luminal pad connector coupled to the fluid conduit at a proximal end. The hub includes a bi-luminal distal hub connector coupled with the pad connector and a bi-luminal proximal hub connector configured to couple with a bi-luminal fluid delivery line (FDL) of a TTM system. The two lumens of the proximal hub connector may be disposed in a concentric arrangement.

In some embodiments, the proximal hub connector includes a pair of valves, where each valve is disposed in line with a separate one of the two lumens. Each valve is configured to automatically prevent fluid flow through its respective lumen upon decoupling of the proximal hub connector from the FDL, and automatically allow fluid flow through its respective lumen upon coupling of the proximal hub connector with the FDL.

The proximal hub connector may be configured to couple with the FDL via a proximal latching mechanism, where the proximal latching mechanism includes a displaceable member. The latching mechanism is configured, such that when the displaceable member is in a displaced state, detachment of the proximal hub connector from the FDL is allowed, and when the displaceable member is in a non-displaced state, detachment of the proximal hub connector from the FDL is prevented.

In some embodiments, each distal hub connector in combination with a corresponding pad connector includes a distal latching mechanism, and at least one of the distal hub connector or pad connector includes a displaceable member of the distal latching mechanism. The distal latching mechanism is configured such that when the displaceable member of the distal latching mechanism is in a displaced state, detachment of the pad connector from the distal hub connector is allowed, and when the displaceable member of the distal latching mechanism is in a non-displaced state, detachment of the pad connector from the distal hub connector is prevented.

The hub may include a plurality of the bi-luminal distal hub connectors, where each distal hub connector is configured to couple with a pad connector, and where each distal hub connector includes a pair of valves. Each valve of the distal hub connector is disposed in line with a separate one of the two lumens, and each valve of the distal hub connector is configured to automatically prevent fluid flow through its respective lumen upon decoupling of the distal hub connector from the pad connector, and automatically allow fluid flow through its respective lumen upon coupling of the distal hub connector with the pad connector.

In some embodiments, the two lumens of the distal hub connector are concentrically arranged. The assembly may further include a plurality of the thermal contact pads coupled with the hub via a plurality of the distal hub connectors. The assembly may further include an authentication tag attached to at least one of the thermal pads or the hub, where the tag is configured to provide authentical data to a TTM module of the TTM system. The hub may include an attachment device configured to couple the hub with at least one of the thermal pad, a bed surface, or a bedrail.

Also disclosed herein is a targeted temperature management (TTM) system including a TTM module configured to provide a TTM fluid. The system further includes a thermal pad configured to facilitate thermal energy transfer between the TTM fluid and a patient, where the pad includes a pad portion configured for placement on the patient and a bi-luminal fluid conduit extending proximally away from the pad portion. The system further includes a bi-liminal fluid delivery line (FDL) configured for transporting TTM fluid between the TTM module and the pad, where the FDL includes a bi-luminal proximal FDL connector at a proximal end of the FDL and a bi-luminal distal FDL connector at a distal end. The system further includes a manifold hub coupled to the FDL at the distal end, where the hub is configured to facilitate a bi-luminal fluid connection between the FDL and the fluid conduit. Coupling of the FDL to the TTM module includes coupling a proximal FDL connector of the FDL to a bi-liminal module connector of the TTM module and opening a pair valves of the TTM module to allow bi-directional flow of the TTM fluid through the module connector, where each valve is disposed in line with a separate one of the two lumens of the module connector. The two lumens of the proximal FDL connector may be concentrically arranged.

The system may further include a connection adapter attached to the TTM module, where the adapter includes the valves and the module connector. The adapter may include an adapter console including a controller having a processor and controller logic stored in memory, and the controller logic is configured to selectively open and close the valves.

The adapter console may further include an authentication module configured to obtain authentication data from an authentication tag attached to at least one of the FDL, the hub or the thermal pad. The controller logic may be configured to open the valves only if the obtained authentication data aligns with authentication information stored in memory.

The adapter may include a latching mechanism configured to secure the proximal FDL connector to the adapter. The latching mechanism includes a pivoting member coupled with the proximal FDL connector so that the proximal FDL connector is rotatable between a horizontal orientation and a vertical orientation. The latching mechanism is further configured, such that when the proximal FDL connector is oriented horizontally, the latching mechanism is deactivated and separation of the proximal FDL connector from the adapter is allowed, and when the proximal FDL connector is oriented vertically, the latching mechanism is activated and separation of the proximal FDL connector from the adapter is prevented.

The latching mechanism may further include a clip configured to engage the proximal FDL connector and thereby constrain the proximal FDL connector in the vertical orientation.

In some embodiments, the manifold hub is coupled to the FDL via a bi-luminal proximal hub connector having a pair of hub valves, where each hub valve is disposed in line with a separate one of the two lumens of the proximal hub connector, and where each hub valve is configured to automatically prevent fluid flow through its respective lumen upon decoupling of the proximal hub connector from the FDL, and automatically allow fluid flow through its respective lumen upon coupling of the proximal hub connector with the FDL.

The proximal hub connector may be configured to couple with the FDL via a proximal latching mechanism, where the proximal latching includes a displaceable member, such that when the displaceable member is in a displaced state, detachment of the proximal hub connector from the FDL is allowed, and when the displaceable member is in a non-displaced state, detachment of the proximal hub connector from the FDL is prevented.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 2 illustrates a hydraulic schematic of the TTM system of FIG. 1B, in accordance with some embodiments.

FIG. 5A illustrates an embodiment of the fluid delivery line (FDL) of FIG. 1B, in accordance with some embodiments.

FIG. 5B illustrates is a cross section view of the fluid delivery line conduit, in accordance with some embodiments.

FIG. 8A illustrates a pad-to-hub connection system having a push-pull mechanism, in accordance with some embodiments.

FIG. 8B illustrates a pad-to-hub connection system where the pad connector includes a displaceable member, in accordance with some embodiments.

FIG. 8C illustrates a pad-to-hub connection system where the hub connector includes a displaceable member, in accordance with some embodiments.

FIG. 8D illustrates a pad-to-hub connection system where the pad connector includes a displaceable shroud, in accordance with some embodiments.

FIG. 8E illustrates a pad-to-hub connection system including an interlocking tooth arrangement, in accordance with some embodiments.

FIG. 8F illustrates the pad-to-hub connection of FIG. 8D in a partially connected state, in accordance with some embodiments.

FIG. 8G illustrates the pad-to-hub connection of FIG. 8D in a fully connected state, in accordance with some embodiments.

FIG. 10A illustrates a manifold hub having a plurality of distal hub connectors disposed in a line, in accordance with some embodiments.

FIG. 10B illustrates the hub of FIG. 10A coupled with a thermal pad, in accordance with some embodiments.

FIG. 10C illustrates the hub of FIG. 10A coupled with a bed surface, in accordance with some embodiments.

FIG. 11A illustrates a manifold hub having a plurality of distal hub connectors disposed along a perimeter of the hub, in accordance with some embodiments.

FIG. 11B illustrates the hub of FIG. 11A disposed on a bed surface, in accordance with some embodiments.

FIG. 11C illustrates the hub of FIG. 11A attached to a thermal pad, in accordance with some embodiments.

FIG. 11D illustrates a back side of the hub of FIG. 11A including an add-on clip, in accordance with some embodiments.

FIG. 11E illustrates the hub of FIG. 11D clipped to a bedrail, in accordance with some embodiments.

DETAILED DESCRIPTION

Figure 1A:
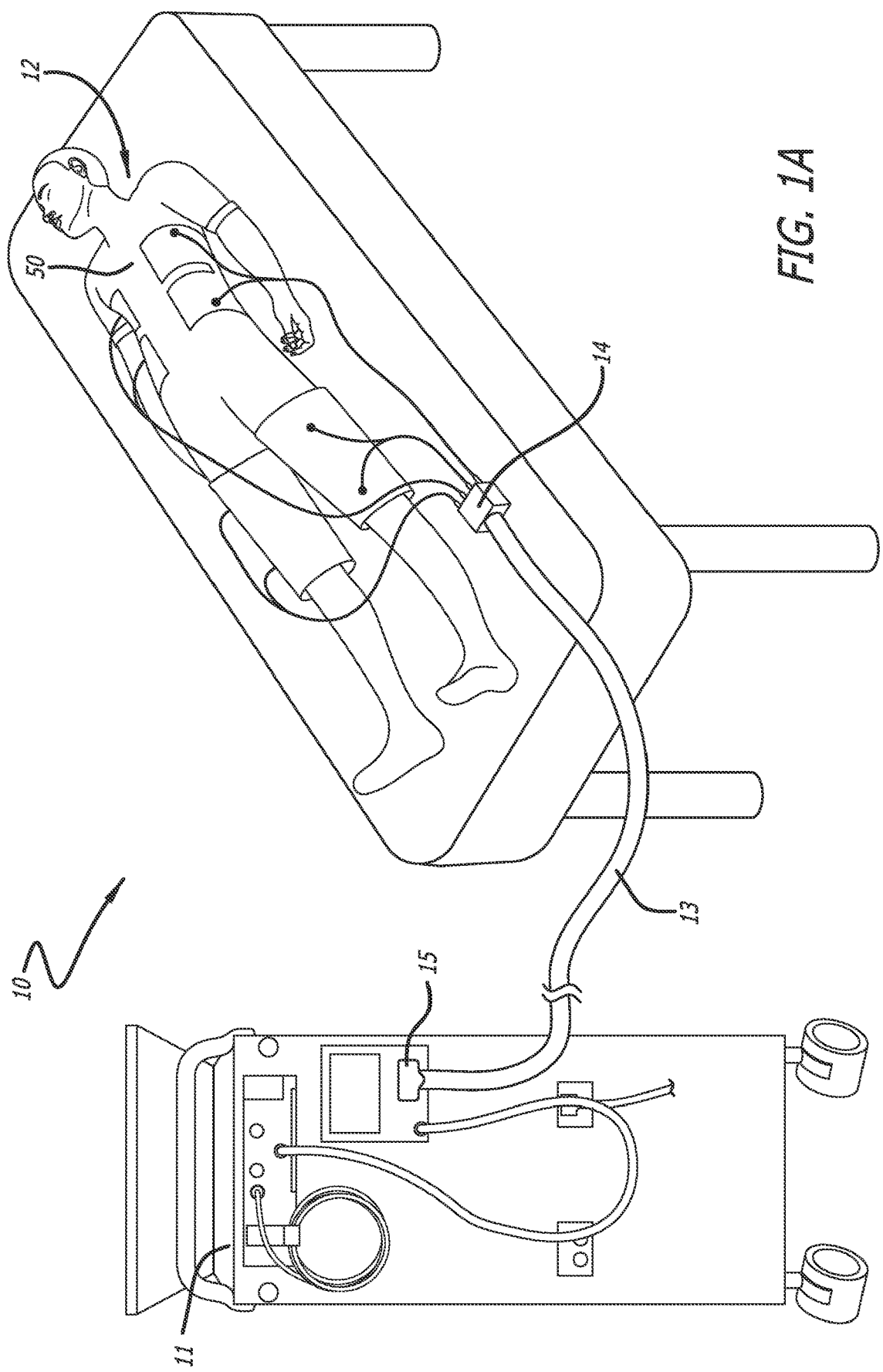
FIG. 1A illustrates a current embodiment of a targeted temperature management (TTM) system for cooling or warming a patient.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," "horizontal," "vertical" and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. The words "including," "has," and "having," as used herein, including the claims, shall have the same meaning as the word "comprising." Furthermore, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The phrases "connected to" and "coupled with" refer to any form of interaction between two or more entities, including mechanical, electrical, magnetic, electromagnetic, fluid, signal, communicative (including wireless), and thermal interaction. Two components may be connected to or coupled with each other even though they are not in direct contact with each other. For example, two components may be coupled with each other through an intermediate component.

The directional terms "proximal" and "distal" are used herein to refer to opposite locations on a medical device. The proximal end of the device is defined as the end of the device closest to the end-user when the device is in use by the end-user. The distal end is the end opposite the proximal end, along the longitudinal direction of the device, or the end furthest from the end-user.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Unless defined otherwise, all technical and scientific terms used herein have the same meaning as commonly understood by those of ordinary skill in the art.

FIG. 1A illustrates a current embodiment of a targeted temperature management (TTM) system 10 for cooling or warming a patient 50. The TTM system 10 includes a TTM module 11, a fluid delivery line (FDL) 13, and a thermal contact pad set 12. The pad set 12 may generally 1, 2, 3, 4, 5, 6, or more thermal contact pads. The fluid delivery 13 provides for transportation of TTM fluid to and from the pad set 12. The FDL 13 may include a hub 14 at a distal end to which multiple thermal pads may be connected.

In some instances, a patient 50 may need to undergo a medical procedure during a TTM therapy session. Some procedures, e.g., an MRI procedure, may necessitate separation of the patient 50 from the TTM module 11. In such instances, it may be advantageous for the thermal pad set 12 to remain in contact with (e.g., applied to) the patient 50 and disconnect the thermal pad set from the FDL 13. To minimize leakage of TTM fluid from the thermal pads and the FDL 13, purging TTM fluid from the thermal pad set 12 and the FDL 13 may be performed. The purging of the TTM fluid may cause an undesirable delay in providing the needed procedure. As such, it may be advantageous to provide a connection system between the hub 14 and the FDL 13 that seals TTM fluid within the pad set 12 and the FDL 13 so that leakage of TTM fluid may be avoided or minimized during disconnection.

In some instances, multiple reuses of the FDL 13 may result is bacterial growth within the FDL 13. As such, the clinician may clean and/or disinfect the FDL 13 at regular intervals, such as before each reuse. In some instances, the reliance on cleaning and disinfecting procedures in a health care environment has shown to be ineffective at reliably preventing patient contamination. To reduce reliance on disinfecting procedures, there is trend away from the reuse of medical devices and toward single use devices.

In further instances, a patient may experience a reduced TTM therapy effect due the use of inferior thermal pads from a third-party manufacture. As such, it may be advantageous to detect an attempted use of an inferior thermal pad prior initiating a TTM therapy. Current technologies, such as radio frequency identification (RFID) tags, make it possible and economically feasible for the piece of capital equipment to check the authenticity of a single use device, such as a thermal pad, and thereby prevent the potential delivery of an ineffective TTM therapy.

In some instances, the connecting of fluid conduits such as the connecting of the fluid delivery line 13 to the TTM module 11 include complexities or difficulties, such as orientation and alignment, that could be eliminated by reconfiguring the connection point therebetween. For example, a side by side arrangement to two fluid conduits may include complexities when making a connection that a coaxial arrangement of the two lumens may avoid.

Figure 1B:
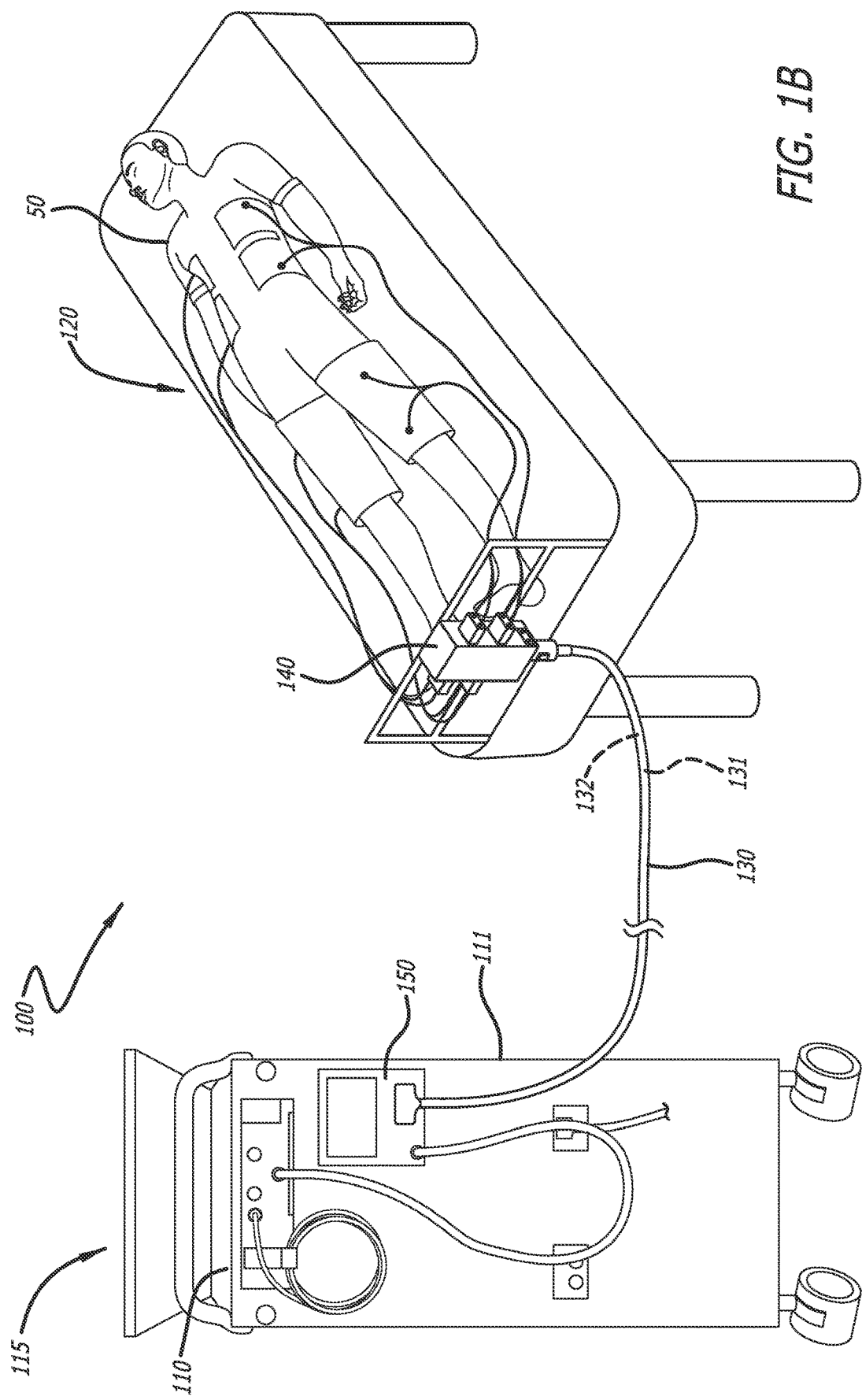
FIG. 1B illustrates an improved targeted temperature management (TTM) system, in accordance with some embodiments.

FIG. 1B illustrates an improved targeted temperature management (TTM) system 100 that may provide enhancements in some of the areas described above. The TTM system 100 includes a TTM module 110, a fluid delivery line (FDL) 130, and a thermal contact pad set 120. In the illustrated embodiment, the pad set 120 includes four thermal contact pads. However, the pad set 120 may include one or more thermal contact pads. The FDL 130 is bi-luminal to facilitate delivery of TTM fluid 112 to the pad set 120 via a fluid delivery lumen 131 and return of TTM fluid 112 to the TTM module 110 via a fluid delivery lumen 132. In the illustrated embodiment, the FDL 130 is coupled with a manifold hub 140. The hub 140 may include one or more distal hub connectors to facilitate fluid coupling to the thermal pads. In one embodiment, the hub 140 includes six distal hub connectors. In the illustrated embodiment of FIG. 1B, the hub 140 includes four distal hub connectors. The hub 140 is also selectively coupled with the FDL 130. Further detailed description of the hub 140 follows below. The system 100 also includes a connection adapter 150 between the FDL 130 and TTM module 110 to provide for an improved fluid connection between the FDL 130 and TTM module 110.

In some embodiments, one or more thermal pads of the pad set 120 may be packaged together with the hub 140 to the define a thermal pad set assembly. In some embodiments of the pad set assembly, the hub 140 may be pre-connected to one or more the thermal pads of the pad set 120.

In use, the TTM module 110 prepares the TTM fluid 112 for delivery to the pad set 120 by heating or cooling the TTM fluid 112 to a defined temperature in accordance with prescribed TTM therapy parameters input by clinician via a graphical user interface 115. The TTM module 110 circulates the TTM fluid 112 between the TTM module 110 and the pad set 120 via the FDL 130. The pad set 120 is applied to the skin 51 of the patient 50 to facilitate thermal energy exchange between the pad set 120 and the patient 50. During the TTM therapy, the TTM module 110 may continually control the temperature of the TTM fluid 112 toward a target TTM temperature.

FIG. 2 illustrates a hydraulic schematic of the TTM system 100. The pad set 120 (FIG. 1B) along with the corresponding fluid conduits are disposed external to the housing 111 of the TTM module 110. The TTM module includes various fluid sensors and fluid control devices to prepare and circulate the TTM fluid 112. The fluid subsystems of the TTM module may include a temperature control subsystem 210 and a circulation subsystem 230.

The temperature control subsystem 210 may include a chiller pump 211 to pump (recirculate) TTM fluid 112 through a chiller circuit 212 that includes a chiller 213 and a chiller tank 214. A temperature sensor 215 within the chiller tank 214 is configured to measure a temperature of the TTM fluid 112 within the chiller tank 214. The chiller 213 may be controlled by a temperature control logic (see FIG. 3) as further described below to establish a desired temperature of the TTM fluid 112 within chiller tank 214. In some instances, the temperature of the TTM fluid 112 within the chiller tank 214 may be less than the target temperature for the TTM therapy.

The temperature control subsystem 210 may further include a mixing pump 221 to pump TTM fluid 112 through a mixing circuit 222 that includes the chiller tank 214, a circulation tank 224, and a dam 228 disposed between the chiller tank 214 and circulation tank 224. The TTM fluid 112, when pumped by the mixing pump 221, enters the chiller tank 214 and mixes with the TTM fluid 112 within the chiller tank 214. The mixed TTM fluid 112 within the chiller tank 214 flows over the dam 228 and into the circulation tank 224. In other words, the mixing circuit 222 mixes the TTM fluid 112 within chiller tank 214 with the TTM fluid 112 within circulation tank 224 to cool the TTM fluid 112 within the circulation tank 224. A temperature sensor 225 within the circulation tank 224 measures the temperature of the TTM fluid 112 within the circulation tank 224. The temperature control logic may control the mixing pump 221 in accordance with temperature data from the temperature sensor 225 within the circulation tank 224.

The circulation tank 224 includes a heater 227 to increase to the temperature of the TTM fluid 112 within the circulation tank 224, and the heater 227 may be controlled by the temperature control logic. In summary, the temperature control logic when executed by the processor (see FIG. 3) may: 1) receive temperature data from the temperature sensor 215 within the chiller tank and the temperature sensor 225 within the circulation tank 224; and 2) control the operation of the chiller 213, the chiller pump 211, the heater 227, and mixing pump 222 to establish and maintain the temperature of the TTM fluid 112 within the circulation tank 224 at the target temperature for the TTM therapy.

The circulation subsystem 230 includes a circulation pump 213 to pull TTM fluid 112 from the circulation tank 224 and through a circulating circuit 232 that includes the pad set 120 located upstream of the circulation pump 213. The circulating circuit 232 also includes a pressure sensor 237 to represent a pressure of the TTM fluid 112 within the pad set 120. The circulating circuit 232 includes a temperature sensor 235 within the circulation tank 224 to represent the temperature of the TTM fluid 112 entering the pad set 120 and a temperature sensor 236 to represent the temperature of the TTM fluid exiting the pad set 120. A flow meter 238 is disposed downstream of the circulation pump 213 to measure the flow rate of TTM fluid 112 through the circulating circuit 232 before the TTM fluid 112 re-enters that the circulation tank 224.

In use, the circulation tank 224, which may be vented to atmosphere, is located below (i.e., at a lower elevation than) the pad set 120 so that a pressure within the pad set 120 is less than atmospheric pressure (i.e., negative) when TTM fluid flow through the circulating circuit 232 is stopped. The pad set 120 is also placed upstream of the circulation pump 231 to further establish a negative pressure within the pad set 120 when the circulation pump 213 is operating. The fluid flow control logic (see FIG. 3) may control the operation of the circulation pump 213 to establish and maintain a desired negative pressure within the pad set 120. A supply tank 240 provides TTM fluid 112 to the circulation tank 224 via a port 241 to maintain a defined volume of TTM fluid 112 within the circulation tank 224.

Figure 3:
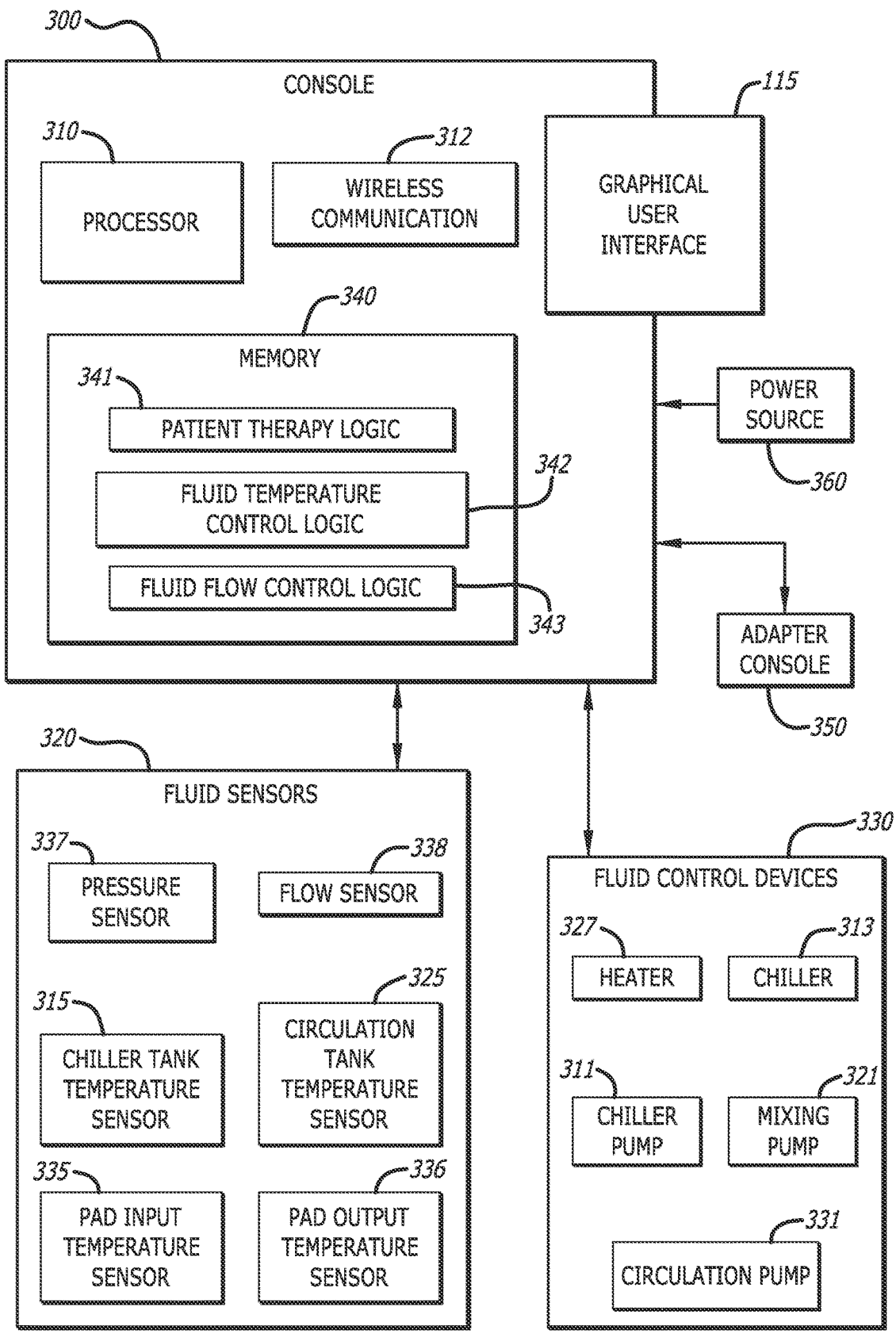
FIG. 3 illustrates a block diagram depicting various elements of a console of the TTM module of FIG. 1B, in accordance with some embodiments.

FIG. 3 illustrates a block diagram depicting various elements of the TTM module 110 of FIG. 1B, in accordance with some embodiments. The TTM module 110 includes a console 300 including a processor 310 and memory 340 including non-transitory, computer-readable medium. Logic modules stored in the memory 340 include patient therapy logic 341, fluid temperature control logic 342, fluid flow control logic 343, and pad identification logic 344. The logic modules when executed by the processor 310 define the operations and functionality of the TTM Module 110.

Illustrated in the block diagram of FIG. 3 are fluid sensors 320 as described above in relation to FIG. 2. Each of the fluid sensors 320 are coupled with the console 300 so that data from the fluid sensors 320 may be utilized in the performance of TTM module operations. Fluid control devices 330 are also illustrated in FIG. 3 as coupled with the console 300. As such, logic modules may control the operation of the fluid control devices 330 as further described below.

The patient therapy logic 341 may receive input from the clinician via the GUI 115 to establish operating parameters in accordance with a prescribed TTM therapy. Operating parameters may include a target temperature for the TTM fluid 112 and/or a thermal energy exchange rate which may include a time-based target temperature profile. In some embodiments, the fluid temperature control logic 342 may define other fluid temperatures of the TTM fluid 112 within the TTM module 110, such a target temperature for the TTM fluid 112 within the chiller tank 214, for example.

The fluid temperature control logic 342 may perform operations to establish and maintain a temperature of the TTM fluid 112 delivered to the pad set 120 in accordance with the predefined target temperature. One temperature control operation may include chilling the TTM fluid 112 within the chiller tank 214. The fluid temperature control logic 342 may utilize temperature data from the chiller tank temperature sensor 215 to control the operation of the chiller 213 to establish and maintain a temperature of the TTM fluid 112 within the chiller tank 214.

Another temperature control operation may include cooling the TTM fluid 112 within the circulation tank 224. The fluid temperature control logic 342 may utilize temperature data from the circulation tank temperature sensor 225 to control the operation of the mixing pump 221 to decrease the temperature of the TTM fluid 112 within the circulation tank 224 by mixing TTM fluid 112 from the chiller tank 214 with TTM fluid 112 within circulation tank 224.

Still another temperature control operation may include warming the TTM fluid 112 within the circulation tank 224. The fluid temperature control logic 342 may utilize temperature data from the circulation tank temperature sensor 225 to control the operation of the heater 227 to increase the temperature of the TTM fluid 112 within the circulation tank 224.

The fluid flow control logic 343 may control the operation of the circulation pump 231. As a thermal energy exchange rate is at least partially defined by the flow rate of the TTM fluid 112 through the pad set 120, the fluid flow control logic 343 may, in some embodiments, control the operation of the circulation pump 231 in accordance with a defined thermal energy exchange rate for the TTM therapy.

The console 300 may include or be coupled with a wireless communication module 312 to facilitate wireless communication with external devices. A power source 360 provides electrical power to the console 300. The console 300 is coupled with the connection adapter console 350 as further described below.

Figure 4A:
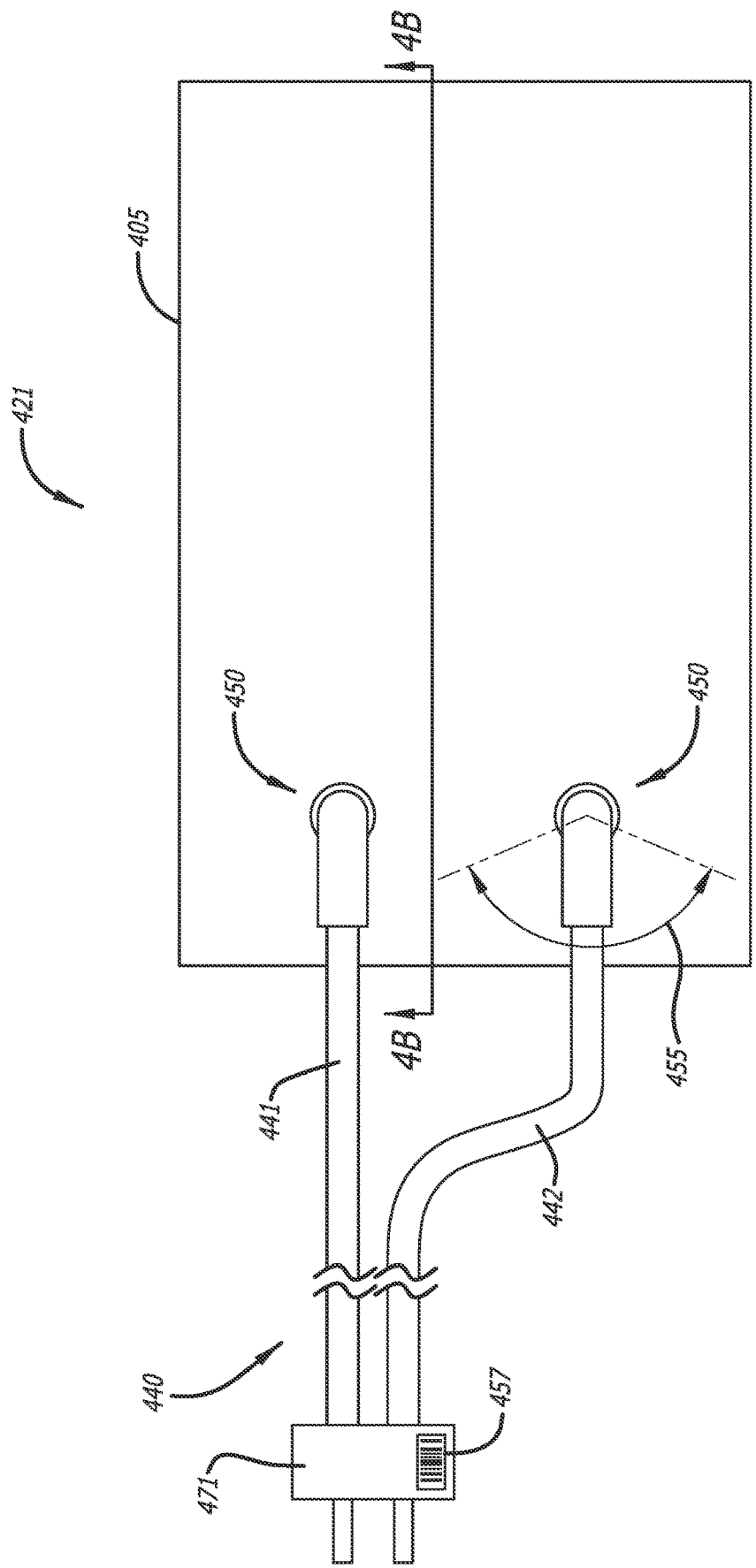
FIG. 4A is a top view of a thermal pad of the system of FIG. 1B, in accordance with some embodiments.

FIG. 4A shows a top view of the thermal contact pad 421 which may be any one pad of the pad set 120. While the description that follows describes features, components and details of the pad 421, the description that follows may equally apply to any and all other thermal contact pads of the pad set 120. The bi-luminal fluid conduit 440 includes a fluid delivery conduit 441 and the fluid return conduit 442 extending proximally away from the joints 450, in accordance with some embodiments. As illustrated, the joints 450 may provide for a rotatable connection between fluid delivery conduit 441 and the fluid return conduit 442 and a pad portion 405 of the pad 421. The rotatable connection may provide for the fluid conduit to rotate through an angle 455 ranging up to about 90 degrees, 180 degrees, 360 degrees, or more. In some embodiments, the joint 450 may define a fixed rotatable connection, i.e., the joint may allow rotation but not separation. In other embodiments, the joint 450 may define a pre-assembled rotatable connection that allows rotation and separation by the clinician. A bi-luminal pad connector 471 is coupled with the fluid conduit 440 at a proximal end of thereof. The pad connector 471 may employ any or all portions the connection system 700 (see FIGS. 7A, 7B below).

In some embodiments, the pad 421 may include an authentication tag 457. The tag 457 may be attached to any portion of the pad 421 such as the connector 471, the fluid conduit 440, or the pad portion 405. The pad authentication tag 457 may be configured to provide pad authentication information or data to a wireless data receiving device as further described below via wireless or wired communications. The authentication information may include pad identification information such as a manufacture's identification. The authentication information may also include product specific information such as a model indication or part number.

Figure 4B:
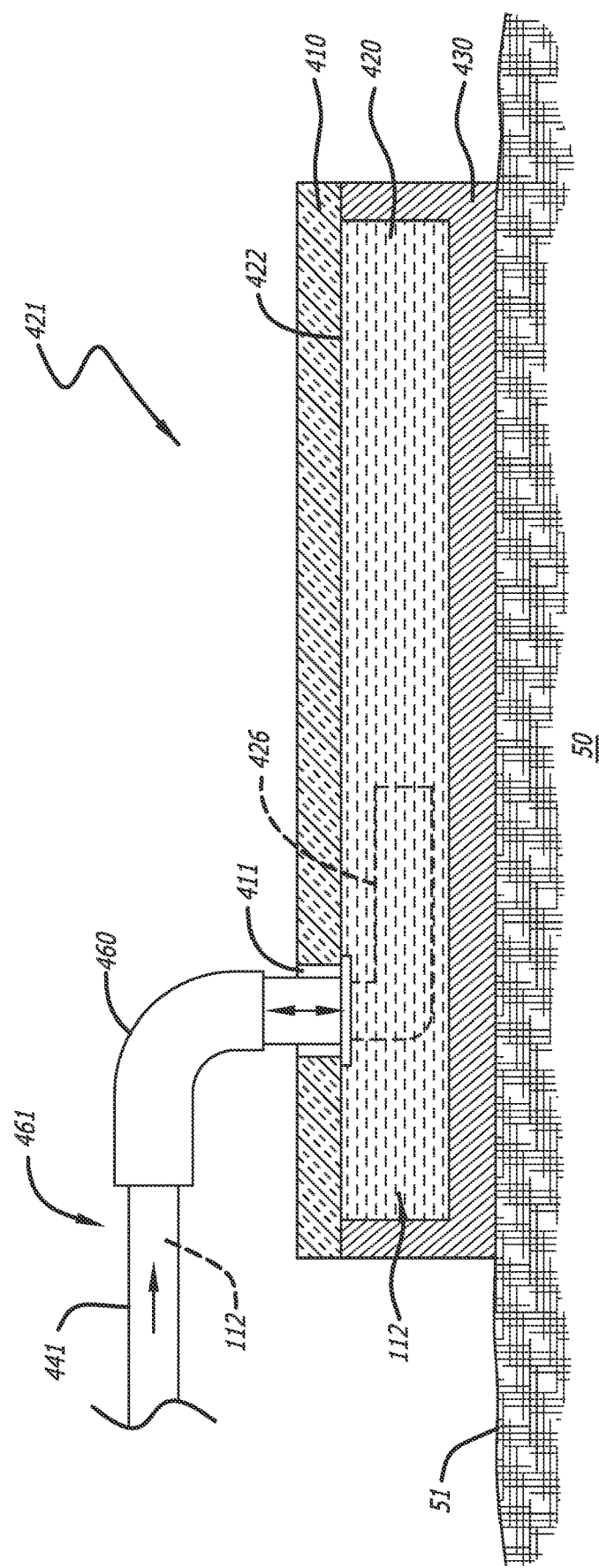
FIG. 4B is a cross-sectional view of the pad of FIG. 4A cut along sectioning lines 4B-4B, in accordance with some embodiments.

FIG. 4B shows a cross-sectional side view of the pad portion 405 of the thermal contact pad 421 of FIG. 4A in contact with the patient 50, in accordance with some embodiments. The pad 421 may include multiple layers to provide multiple functions of the pad 421. A fluid containing layer 420 is fluidly coupled with the fluid delivery conduit 441 via the joint 450 to facilitate circulation of the TTM fluid 112 within the fluid containing layer 420. Similarly, (although not shown in FIG. 4B) the fluid containing layer 420 is fluidly coupled with the fluid return conduit 442 via the joint 450. The fluid containing layer 420 having TTM fluid 112 circulating therein defines a heat sink or a heat source for the patient 50 in accordance with a temperature of the TTM fluid 112. The fluid delivery conduit 441 may also be coupled with an internal fluid conduit 426 of the fluid containing layer 420 so that TTM fluid 112 entering the fluid containing layer 420 passes through the internal fluid conduit 426.

The pad 421 may include a thermal conduction layer 430 disposed between the fluid containing layer 420 and the patient 50. The thermal conduction layer 430 is configured to facilitate thermal energy transfer between the fluid containing layer 420 and the patient 50. The thermal conduction layer 430 may be attached to the thermal conduction layer 430 along a bottom surface 421 of the fluid containing layer 420. The thermal conduction layer 430 may be conformable to provide for intimate contact with the patient 50. In other words, thermal conduction layer 430 may conform to a contour of the patient 50 to inhibit the presence space or air pockets between the thermal conduction layer 430 and the patient 50.

The pad 421 may include an insulation layer 410 disposed on the top side of the fluid containing layer 420. The insulation layer 410 is configured to inhibit thermal energy transfer between the fluid containing layer 420 and the environment. The insulation layer 410 may be attached to the fluid containing layer 420 along a top surface 422 of the fluid containing layer 420. In some embodiments, the insulation layer 410 may include one or more openings 411 extending through the insulation layer 410 to provide for coupling of the fluid delivery conduit 441 and fluid return conduit 442 with the fluid containing layer 420.

The joint 450 may include an elbow 460 to change the orientation of the fluid delivery conduit 441 extending away from the joint 450. As shown, the orientation of the fluid delivery conduit 441 is shifted from an orientation perpendicular to the pad 421 to an orientation that is substantially parallel to the pad 421. The elbow 460 also establishes an orientation of a distal portion 461 of the fluid delivery conduit 441 to be substantially parallel to the pad 421 and/or the fluid containing layer 420.

FIG. 5A illustrates an embodiment of the fluid delivery line 130 and associated features and components coupled to the manifold hub 140. The FDL 130 includes a proximal FDL connector 532 for coupling with the adapter 150, a distal FDL connector 533 for coupling with the manifold hub 140, and a bi-luminal FDL conduit 531 extending from the proximal FDL connector 532 to the distal FDL connector 533. The hub 140 includes a proximal hub connector 543 configured to couple with the distal FDL connector 533. The hub 140 also includes one or more distal hub connectors 571 for connecting to the thermal pad set 120. Each distal hub connector 571 is configured for coupling with a corresponding pad connector 471. In some embodiments, the distal hub connectors 571 may be disposed on opposite sides of the hub 140. In the illustrated embodiment of FIG. 5A, three distal hub connectors 571 are disposed on opposing sides of the hub 140. The distal hub connectors 571 may be oriented so that the fluid conduits 440 of the thermal pads extend away from opposite sides of the hub 140 in a direction perpendicular to the FDL conduit 531. The distal hub connectors 571, the proximal hub connector 543, the distal FDL connector 533, and the proximal FDL connector 532 may employ any or all portions the connection system 700 (see FIGS. 7A, 7B below).

The FDL 130 may include an FDL authentication tag 557 attached thereto. The FDL authentication tag 557 may be attached to any portion of the FDL 130 such as the proximal FDL connector 532 (as shown), the FDL conduit 531, or the distal FDL connector 533. The FDL authentication tag 557 may be configured to provide FDL authentication information further described below. The FDL authentication information may include FDL identification information such as a manufacture's identification. The FDL authentication information may also include product specific information such as an FDL model indication or an FDL part number. In some embodiments, the FDL authentication information may include manufacturing information such as a manufacturing date range or a lot number. As discussed below with respect to FIGS. 9A-9D, the connectors 532, 533 and the FDL conduit 531 may include wiring 535 coupled thereto extending the length of the FDL 130.

In some embodiments, the hub 140 may include a hub authentication tag 547 attached thereto. The hub authentication tag 547 may be configured to wirelessly provide hub authentication information or data to a wireless data receiving device as further described below. The hub authentication information may include hub identification information such as a manufacture's identification. The hub authentication information may also include product specific information such as a hub model indication or a hub part number. In some embodiments, the hub authentication information may include manufacturing information such as a manufacturing date range or a lot number. In some embodiments, the hub authentication tag 547 may be a radio frequency identification (RFID) tag.

FIG. 5B illustrates is a cross section view of the FDL conduit 531. In some embodiments, the two lumens of the FDL conduit 531 may be disposed in a concentric arrangement. As shown in FIG. 5B, a fluid delivery lumen 534A may be disposed within the fluid return lumen 534B. Such an arrangement may facilitate equal flexibility of the FDL conduit 531 in all directions. The concentric arrangement may also minimize a change in temperature of the TTM fluid 112 as it flows through the fluid delivery lumen 534 toward the patient 50. In other embodiments, the two lumens of the FDL conduit 531 may be disposed in a side-by-side arrangement.

Figure 5C:
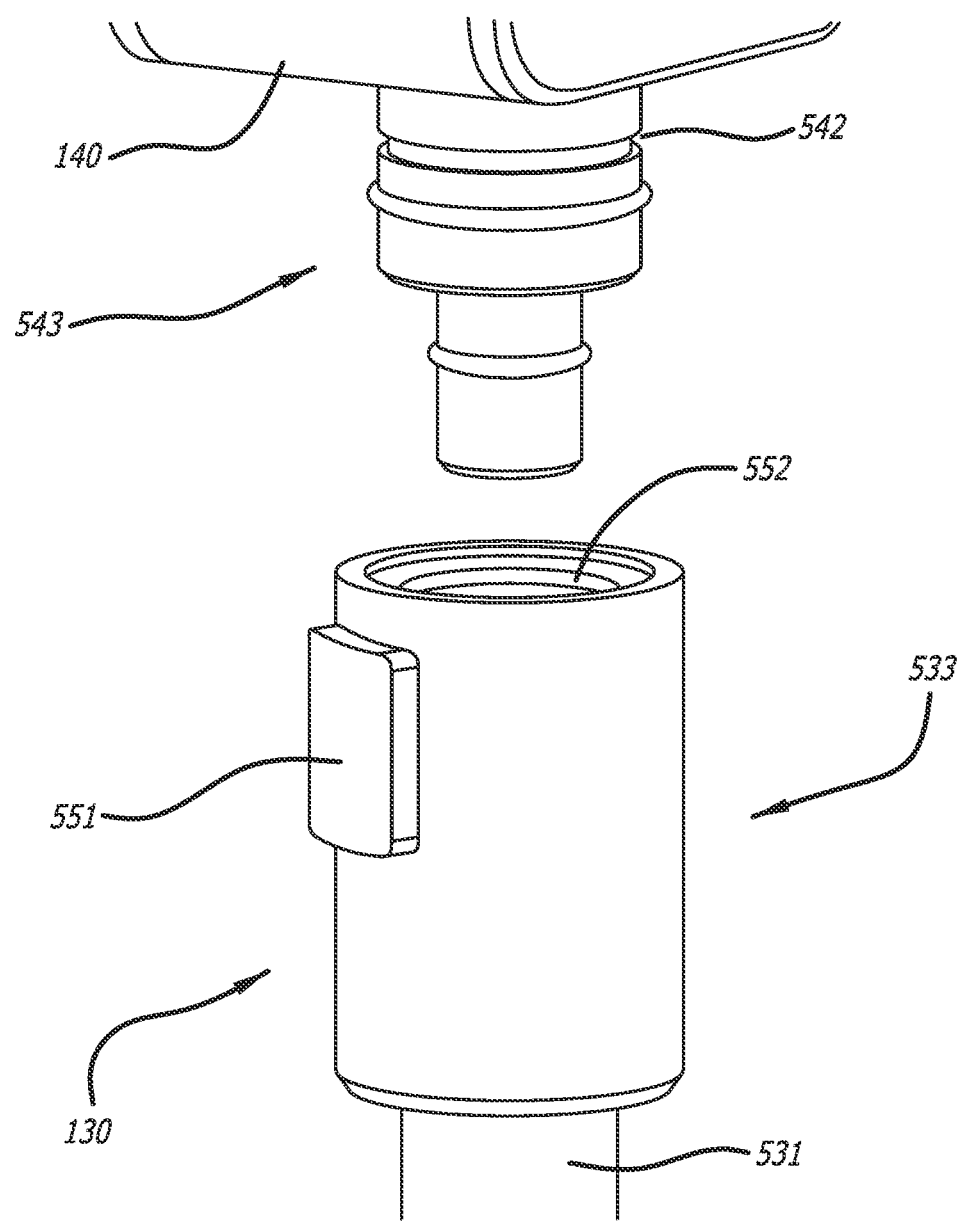
FIG. 5C illustrates an FDL-to-hub connection system where an FDL connector includes a displaceable latch member, in accordance with some embodiments.

FIG. 5C illustrates an FDL-to-hub connection system including the distal FDL connector 533 and the proximal hub connector 543. The distal FDL connector 533 and the proximal hub connector 543 may facilitate selective connection and disconnection of the FDL 130 to and from the hub 140. Each of the distal FDL connector 533 and the proximal hub connector 543 are bi-luminal connectors facilitating bi-direction flow of TTM fluid therethrough. As shown, the arrangement of the two lumens at the point of connection is concentric so that the distal FDL connector 533 and the proximal hub connector 543 may be rotated relative to each other while maintaining bi-direction flow of TTM fluid therethrough. The concentric luminal arrangement also facilitates coupling of the distal FDL connector 533 with the proximal hub connector 543 at any relative angular orientation therebetween. The distal FDL connector 533 and the proximal hub connector 543 may employ any or all portions the connection system 700 (see FIGS. 7A, 7B below). In some embodiments, the distal FDL connector 533 and the proximal hub connector 543 may be omitted such that the FDL conduit 531 is fixedly coupled to the hub 140.

The FDL-to-hub connection system may also include a latching mechanism to prevent inadvertent separation of the distal FDL connector 533 from the proximal hub connector 543. In the illustrated embodiment, the FDL-to-hub connection system includes an exemplary ring-in-groove latching mechanism where a ring 552 of the distal FDL connector 533 is selectively engaged with a groove 542 of the proximal hub connector 543. In other words, when the distal FDL connector 533 and the proximal hub connector 543 are coupled together, the ring 552 may be disposed within the groove 542 and thereby prevent displacement of the FDL connector 533 away from the proximal hub connector 543. In the illustrated embodiment, the ring 552 may be biased toward engagement with the groove 542.

The ring 552 is operatively coupled with a displaceable member (or button) 551 so that when the button 551 is depressed, the ring 552 is disengaged from the groove 542, thereby allowing separation of the distal FDL connector 533 from the proximal hub connector 543. In use, the clinician may depress the button 551 during coupling and/or decoupling of the connectors 533, 543 with each other.

Figure 6:
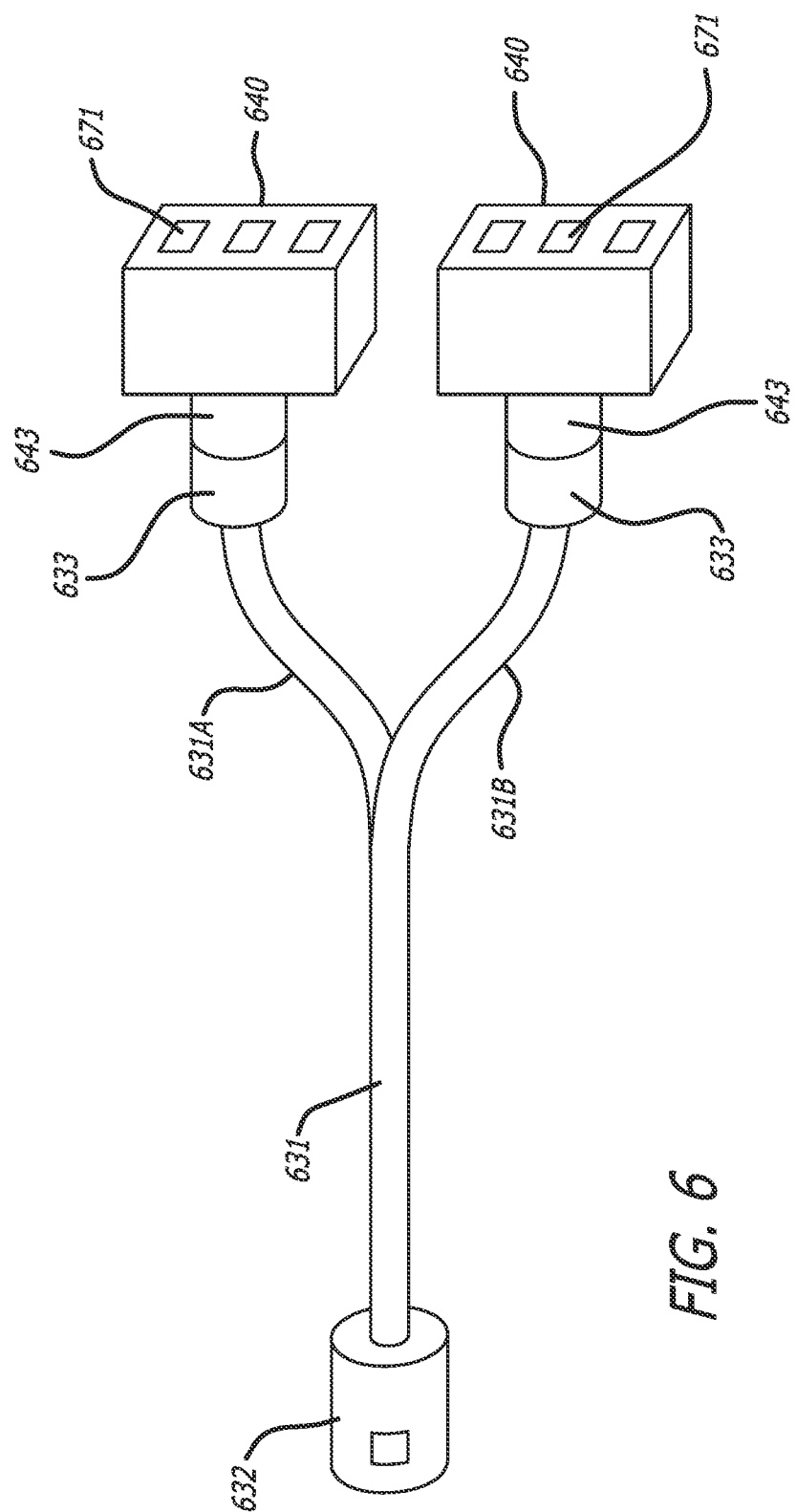
FIG. 6 illustrates an embodiment of a bifurcated fluid delivery line, in accordance with some embodiments.

FIG. 6 illustrates an embodiment of an FDL 630 having a proximal FDL connector 632 at a proximal end and bifurcated FDL conduit 631 defining FDL legs 631A, 631B. In the illustrated embodiment, the FDL 630 couples to two manifold hubs 640. Each leg includes a distal FDL connector 633 coupled to the proximal hub connector 643 of each hub 640. Each proximal hub connector 643 is selectively coupled to the corresponding distal FDL connector 633. The distal hub connectors 671, the proximal hub connector 643, the distal FDL connector 633, and the proximal FDL connector 632 may employ any or all portions the connection system 700 (see FIGS. 7A, 7B below). In some embodiments, the distal FDL connectors 633 and the proximal hub connectors 643 may be omitted such that the FDL conduit 631 is fixedly coupled to the hubs 640.

The bifurcated FDL 630 may provide for enhanced placement of the FDL 630 and the fluid conduits 440 (FIG. 4A) of each pad of the pad set 120. For example, the leg 631A along with its associated hub 640 may be placed along one side of the patient 50, where the hub 640 may be coupled to the three of the six thermal pads of the pad set 120. The other leg 631B along with its associated hub 640 may be placed along the other side of the patient 50, where it may be coupled to the other three of the six thermal pads of the pad set 120. In some embodiments, the hubs 640 may be attached directly and permanently to FDL legs 631A, 631B. In such embodiments, the distal FDL connectors 633 and the proximal hub connectors 643 may be omitted.

Figure 7A:
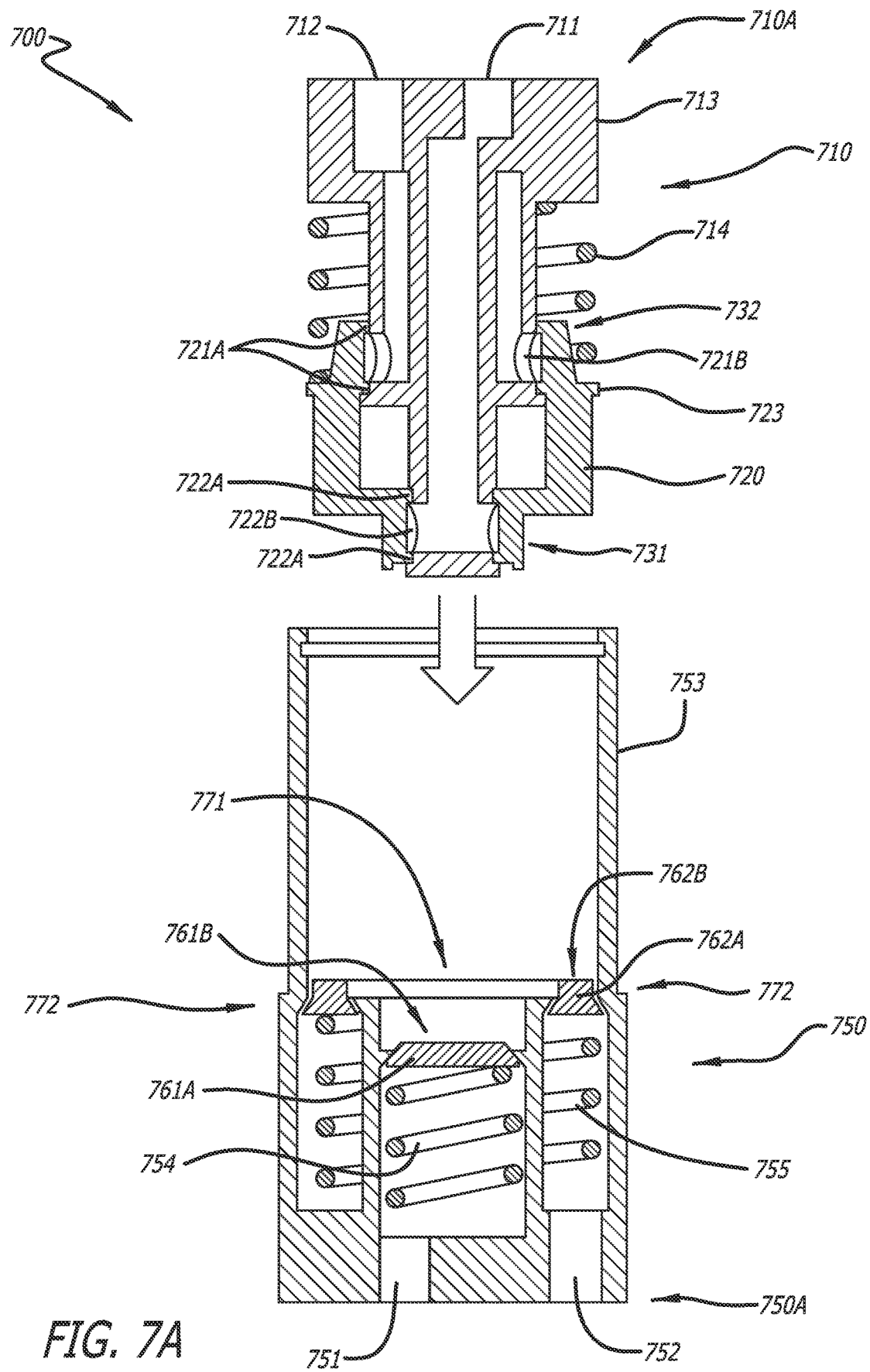
FIG. 7A illustrates a coaxial bi-luminal connection system in a disconnected state, the connection system including valves, in accordance with some embodiments.
Figure 7B:
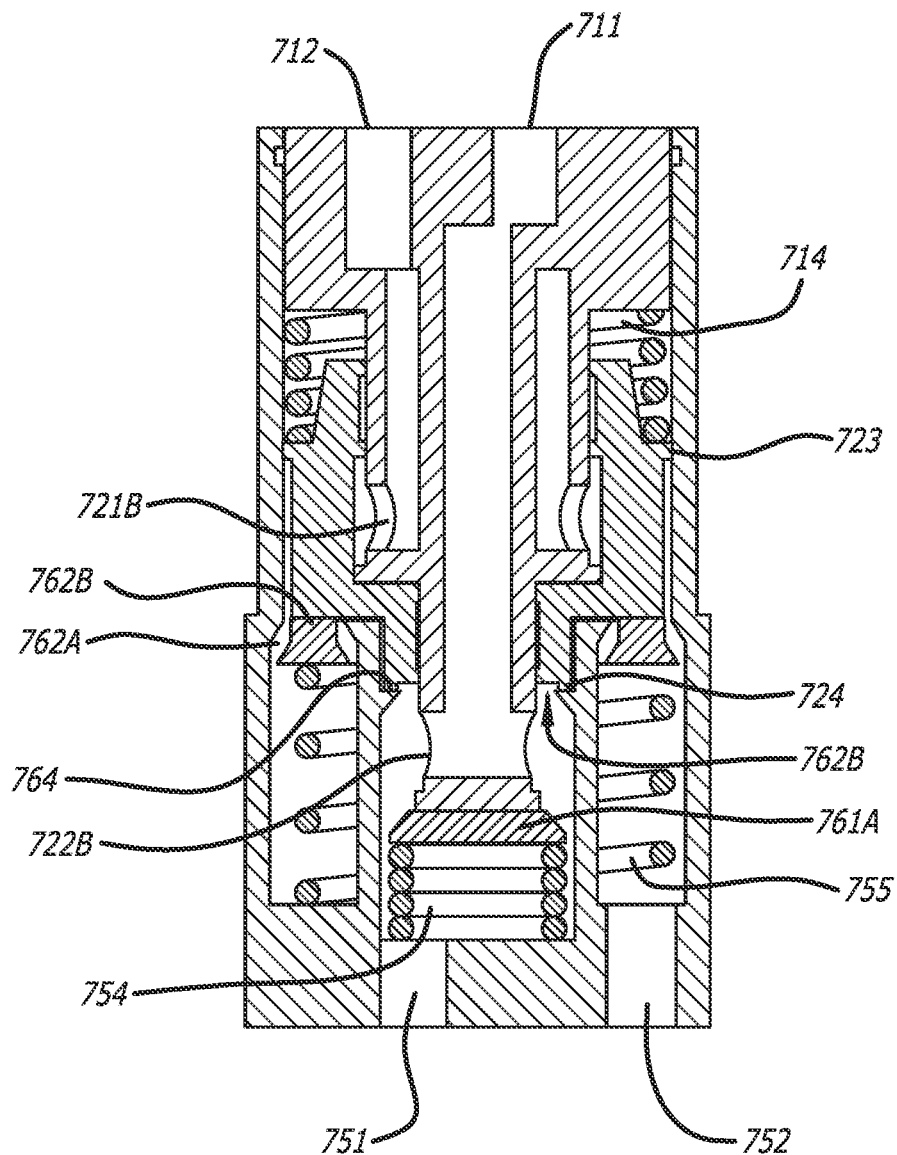
FIG. 7B illustrates the connection system of FIG. 7A in a connected state, in accordance with some embodiments.

FIGS. 7A and 7B illustrate a bi-luminal connection system 700 including a first connector 710 and a second connector 750. FIG. 7A shows cross-sectional views of the first connector 710 and the second connector 750 of the connection system 700 in a disconnected state and FIG. 7B shows similar cross-sectional views of the connection system 700 in a connected state.

The connection system 700 is configured for connecting bi-luminal fluid conduits together so that bi-directional fluid flow through the bi-luminal fluid conduits is maintained across the connection system 700. The first connector 710 includes a first delivery lumen 711 and a first return lumen 712, and the second connector 750 includes a second delivery lumen 751 and a second return lumen 752. The connection system 700 is configured so that when the first connector 710 is coupled with the second connector 750, the first delivery lumen 711 is in fluid communication with the second delivery lumen 751 and the first return lumen 712 is in fluid communication with the second return lumen 752. As shown, the fluid delivery lumens 711, 751 are concentrically disposed within the annular fluid return lumens 712, 752 at the point of connection.

As also shown, the first delivery lumen 711 and the first return lumen 712 may be disposed in a side-by-side arrangement at a conduit coupling end 710A of the first connector 710. As such, the first connector 710 is configured to couple with a bi-luminal fluid conduit having fluid lumens arranged side-by-side. As may be appreciated by one of ordinary skill, the side-by-side arrangement of the first delivery lumen 711 and the first return lumen 712 is also compatible with coupling of the first connector 710 with a bi-luminal fluid conduit having concentrically arranged fluid lumens, where the first delivery lumen 711 is coupled with a central lumen of the fluid conduit and the first return lumen 712 is coupled with an annular lumen of the fluid conduit. Similarly, a conduit coupling end 750A the second connector 750 is configured to couple with a bi-luminal fluid conduit having fluid lumens disposed in a side-by-side or a concentric arrangement.

The connection system 700 is also configured to prevent fluid flow through the first and second delivery lumens 711, 751 and the first and second return lumens 712, 752 when the second connector 750 is disconnected from the first connector 710. The connection system 700 is also configured to minimize dripping of TTM fluid from the connectors 710, 750 upon disconnection of the connectors 710, 750 from each other. The first connector 710 includes a first delivery valve 731 to close off the first delivery lumen 711 upon disconnection of the first connector 710. The first connector 710 further includes a first return valve 732 to close off the first return lumen 712 upon disconnection of the first connector 710. By way of summary, when the first connector 710 is disconnected from the second connector 750, fluid flow through the first connecter 710 is prevented. The first delivery valve 731 and the first return valve 732 are biased toward the closed state, so that the valves 731, 732 automatically close upon disconnection.

The second connector 750 includes a second delivery valve 771 to close off the second delivery lumen 751 upon disconnection of the second connector 750. The second connector 750 further includes a second return valve 772 to close off the second return lumen 752 upon disconnection of the second connector 750. By way of summary, when the second connector 750 is disconnected from the first connector 710, a fluid flow through the second connecter 750 is prevented. The second delivery valve 771 and the second return valve 772 are also biased toward the closed state, so that the valves 771, 772 automatically close upon disconnection.

The first and second connectors 710, 750 include various structural elements. The first connector 710 and the second connector 750 include connector housings 713, 753, respectively. The first connector 710 includes a sealing member 720 configured to perform various sealing functions of the first connector 710. The sealing member 720 or one or more portions thereof, may be formed of a deformable material such as an elastomeric material to define multiple fluid seals with corresponding sealing surfaces of the first connector housing 713 and the second connector housing 753. The sealing member 720 is displaceable between a bottom position when the first connector 710 is in the disconnected state as shown in FIG. 7A and a top position when the first connector 710 is in the connected state as shown in FIG. 7B. In the illustrated embodiment, the connection system 700 includes one and only one sealing element 720 to define fluid seals between the connectors 710, 750.

The sealing member 720 includes first delivery valve sealing elements 722A configured to cover and seal off one or more first delivery valve side ports 722B when the sealing member 720 is the bottom position. When the sealing member 720 is in the top position, the first delivery valve sealing elements 722A are displaced away from the first delivery valve side port 722B to uncover the first delivery valve side port 722B thereby opening the first delivery valve 731.

The sealing member 720 includes first return valve sealing elements 721A configured to cover and seal off one or more first return valve side ports 721B when the sealing member 720 is the bottom position. When the sealing member 720 is in the top position, the first return valve sealing elements 721A are displaced away from the first return valve side port 721B to uncover the first return valve side port 721B thereby opening the first return valve 732.

The sealing member 720 includes an outer connector sealing element 723 to define a seal with the second connector housing 753. The connection system 700 is configured so that, during the coupling process of the first connector 710 with the second connector 750, the outer sealing element 723 forms a seal with the second connector housing 753 before any of the valves 731, 732, 771, or 772 are opened to prevent leaking of TTM fluid 112 during the coupling process. Similarly, during disconnection all of the valves 731, 732, 771, and 772 are closed prior to decoupling the outer connector sealing element 723 from the second connector housing 753 to prevent leaking of TTM fluid 112 during the decoupling process. The sealing member 720 further includes an inner connector sealing element 724 to define a seal with the annular ledge 764 of the second connector 750. The first connector 710 includes a biasing member 714 to exert a biasing force on the sealing member 720 toward the bottom position. In some embodiments, the biasing member 714 may be coil spring formed of a metal or non-metal material. Other forms of the biasing member 714 such as deflectable portions of the first connector housing 713 or the sealing member 720 are also contemplated and disclosed herein.

The second connector 750 includes a second delivery valve disk 761A and a corresponding second delivery valve port 761B. The second delivery valve disk 761A and the corresponding second delivery valve port 761B combine to define a poppet style valve. The second delivery valve disk 761A is displaceable between a top position when the second connector 750 is in the disconnected state as shown in FIG. 7A and a bottom position when the second connector 750 is in the connected state as shown in FIG. 7B. A biasing member 754 exerts a force on the second delivery valve disk 761A toward to the second delivery valve port 761B to bias the second delivery valve 771 toward the closed state. Interaction between the first connector housing 713 and the second delivery valve disk 761A displaces the second delivery valve disk 761A downward to the bottom position to open the second delivery valve 771. The second delivery valve disk 761A or a portion thereof may be formed of a deformable material such as an elastomeric material to define fluid seal with the second delivery valve port 761B. In some embodiments, the biasing member 754 may be coil spring formed of a metal or non-metal material. Other forms of the biasing member 754 such as deflectable portions of the second connector housing 753 or the second delivery valve disk 761A are also contemplated and disclosed herein.

The second connector 750 further includes a second return valve sealing ring 762A and a corresponding second return valve annular port 762B. The sealing ring 762A and the annular port 762B combine to define an annular poppet style valve. The sealing ring 762A is displaceable between a top position when the second connector 750 is in the disconnected state as shown in FIG. 7A and a bottom position when the second connector 750 is in the connected state as shown in FIG. 7B. A biasing member 755 exerts a force on the second sealing ring 762A toward to the annular port 762B to bias the second delivery return valve 772 toward the closed state. Interaction between the sealing member 720 and the sealing ring 762A displaces the sealing ring 762A downward to the bottom position to open the second delivery valve 772. The sealing ring 762A or a portion thereof may be formed of a deformable material such as an elastomeric material to define a fluid seal with the annular port 762B. In some embodiments, the biasing member 755 may be coil spring formed of a metal or non-metal material. Other forms of the biasing member 755 such as deflectable portions of the second connector housing 753 or the sealing ring 762A are also contemplated and disclosed herein.

The bi-luminal connection system 700 or portions thereof may be employed with the TTM system 100 to define a fluid connection between any two fluid connection entities. For example, the connection system 700 or portions may be employed where the FDL 130 is connected to the connection adapter 150, where the FDL 130 is connected to the hub 140, or where the fluid conduits 440 of the pad set 120 are connected to the hub 140. In some embodiments, only a portion of the connection system 700 may be employed, such as one or more of the first delivery valve 731, the first return valve 732, the second delivery valve 771, or the second return valve 772. Similarly, in some embodiments, the first connector 710 or the second connector 750 may be attached to a bi-luminal fluid conduit having the two lumens arranged concentrically.

FIGS. 8A-8G illustrate various embodiments of a pad-to-hub latching mechanism including a displaceable member configured to deactivate and/or activate the latching mechanism. FIG. 8A illustrates a latching mechanism 871 for securing the pad connector 811 to the hub 841. The pad connector 811 includes a displaceable member 812 attached to the fluid conduit 440. The displaceable member 812 defines a push-pull function of the latching mechanism 871 so that when the displaceable member 812 is displaced toward the hub 841, the pad connector 811 may be separated from the hub 841 by pulling on the connector 811. Corresponding components and structure within the connector 811 and the hub 841 define an overlapping (or interfering) engagement between a portion of the connector 811 and a portion of the hub 841, where the engagement prevents separating displacement of the connector 811 with respect to the hub 841. In use, to disconnect the pad connector 811 from the hub 841, the clinician may push the displaceable member 812 toward the hub 841 to deactivate the latching mechanism 871 and thereafter separate the pad connector 811 from the hub 841 by pulling on the housing of the connector 811. To connect the pad connector 811 to the hub 841, the clinician may push the displaceable member 812 toward the housing of the pad connector 811 to deactivate the latching mechanism 871 and thereafter displace the pad connector 811 toward the hub 841. In some embodiments of use, the clinician may push the displaceable member 812 toward the hub 841 to deactivate the latching mechanism 871 and displace the pad connector 811 toward the hub 841 in a single step.

FIG. 8B illustrates a latching mechanism 872 for securing the pad connector 813 to the hub 842. The pad connector 813 includes a displaceable (or deflectable) member 814 pivotably attached to the housing 813A of the pad connector 813. The displaceable member 814 defines a lateral displacement function of the latching mechanism 871, i.e., the displaceable member 814 is moved in a substantially perpendicular direction with respect to the displacement direction of the pad connector 813 when connecting and disconnecting the pad connector 813 to the hub 842. The displaceable member 814 is coupled the connector housing 813A via a bendable hinge portion of the displaceable member 814, such that the bendable hinge portion bends when the displaceable member 814 is displaced toward the housing 813A. Corresponding structure of the displaceable member 814 and the hub define an overlapping (or interfering) engagement between a portion of the displaceable member 814 and a portion of the hub 841 during use. To connect the pad connector 811 to the hub 842, the clinician displaces the displaceable member 814 toward the housing 813A and thereafter connects the pad connector 811 to the hub 842 thereby establishing the fluid connection. Once connected, the clinician allows the displaceable member 814 to self-deflect away from the housing 813A resulting in the overlapping engagement of the portion of the displaceable member 814 and the portion of the hub 842 to secure the pad connector 813 to the hub 842. To disconnect the pad connector 811 from the hub 842, the clinician displaces the displaceable member 814 toward the housing 813A to defeat the overlapping engagement, thereby allow separation of the pad connector 811 away from the hub 842.

FIG. 8C illustrates a pad-to-hub latching mechanism 873 for securing the pad connector 815 to the hub 843. The hub 843 includes a displaceable member (or button) 816. Corresponding components and structure of the connector 815 and the hub 843 establish an overlapping (or interfering) engagement between a portion of the connector 815 and a portion of the hub 842 to define the latching mechanism 873. In use, to disconnect the pad connector 815 from the hub 843, the clinician depresses the button to deactivate the latching mechanism 873, i.e., to disengage the overlapping portions. Thereafter, the clinician may separate the pad connector 815 away from the hub 843. To connect the pad connector 815 to the hub 843, the clinician depresses the button 816 to deactivate the latching mechanism 873 and thereafter connects the pad connector 815 to the hub 843 thereby establishing the fluid connection. Once connected, the clinician releases to the button 816 to activate latching mechanism 873.

FIG. 8D illustrates a pad-to-hub latching mechanism 874 where the pad connector 817 includes a displaceable shroud 818. Corresponding components and structure of the connector 817 and the hub 844 establish an overlapping (or interfering) engagement between an internal portion of the connector 817 and one or more protrusions 845 extending away from the hub 844 to define the latching mechanism 874. The latching mechanism 874 is configured so that displacing the shroud 818 away from the hub 844 (as shown by the arrow 875) in opposition to a biasing force (not shown), deactivates the latching mechanism 874, and allowing the shroud 818 to self-displace, due to the biasing force, toward the hub 844, activates the latching mechanism 874. In use, the clinician may grasp the fluid conduits 440 with one or more of the middle finger, ring finger, and pinky of one hand while simultaneously grasping the shroud 818 with the thumb and forefinger of the same hand, to distally displace the shroud 818. To disconnect the pad connector 817 from the hub 844, the clinician may displace the shroud 818 to deactivate the latching mechanism 874 and thereafter, separate the pad connector 817 from the hub 844. To connect the pad connector 817 to the hub 844, the clinician may displace the shroud 818 and thereafter connect the pad connector 817 to the hub 844. In some embodiments, the latching mechanism 874 may be configured to self-deactivate while connecting the pad connector 817 to the hub 844, thereby facilitating connection via a single step.

FIG. 8E-8G illustrate a pad-to-hub latching mechanism 875. FIG. 8E shows the pad connector 819 separated from the hub 845, FIG. 8F shows the pad connector 819 partially engaged with the hub 845, and FIG. 8G is shows the pad connector 819 and the hub 845 in a fully latched state. As shown in FIG. 8E, the hub 845 is configured to receive the pad connector 819 within a slot 845C. FIG. 8E illustrates that insertion of the pad connecter 819 into the slot 845C is performed with the pad connector 819 disposed at an angle 846 with respect to the hub 845 so that the curved end 819A of the pad connector 819 may fit within the jaw 845A of the hub 845. Once the curved end 819A is within the jaw 845A, the pad connector 819 is rotated until the pad connector 819 is oriented parallel to the hub 845 to lock the curved end 819A within the jaw 845A as shown in FIG. 8G. The connector 819 and the hub 845 further include corresponding teeth 819B, 845B, respectively that engage each other when the pad connector 819 is oriented parallel to the hub 845 to fully latch the pad connector 819 to the hub 845. Upon connection of the pad connector 819 to the hub 845, flow of TTM fluid 112 is facilitated from the FDL 130 through the hub 845 and pad connector 819 to fluid conduits 440. In use, to connect the pad connector 819 to the hub 845, the clinician orients the pad connector 819 at the angle 846 and then inserts the pad connector 819 into the slot 845C until the curved end 819A is engaged in the jaw 845A. The clinician then rotates the pad connector 819 into the fully latched position. To disconnect the connector 819 from the hub 845, the clinician anti-rotates the pad connector to the angle 846 and then separates the pad connector 819 from the hub 845.

Figure 9A:
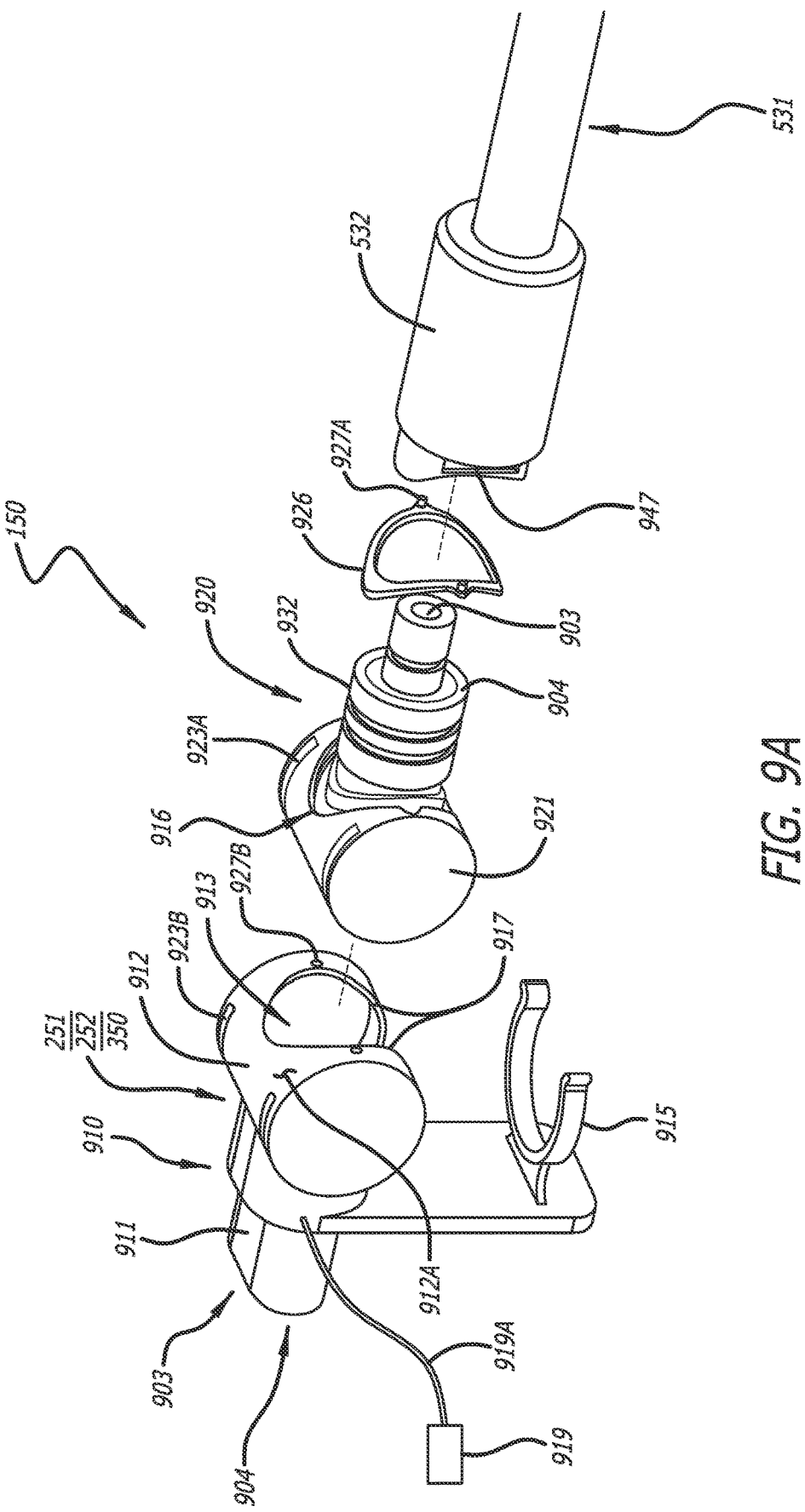
FIG. 9A illustrates the module-to-FDL connection adapter of FIG. 1B, in accordance with some embodiments.

FIGS. 9A-9D show various illustrations of the module-to-FDL connection adapter 150. FIG. 9A illustrates an exploded view of the module-to-FDL connection adapter 150. The adapter 150 is configured for attachment to the TTM module 110 at a customer location such as a healthcare facility. The adapter 150 is further configured to convert the module connector 15 (FIG. 1A), which is compatible with the FDL 13, to the adapter connector 932 which is compatible with the proximal FDL connector 532 of the FDL 130. The adapter 150 includes an input connector 911 compatible with the module connector 15. In use, the adapter 150 is attached to the TTM module 110 to replace the module connector 15.

The adapter 150 is bi-luminal including a delivery lumen 903 extending from the input connector 911 to the adapter connector 932 and a return lumen 904 also extending from the input connector 911 to the adapter connector 932. In the illustrated embodiment, the adapter connector 932 defines a male connecting portion and the proximal FDL connector 532 defines a female connecting portion. In other embodiments, the adapter connector 932 may define a female connecting portion and the proximal FDL connector 532 may define a male connecting portion.

The adapter 150 defines a housing 910 including a hollow cylindrical portion 912. The housing 910 may enclose various components as further described below. The adapter 150 further includes a rotatable member 920 including the adapter connector 932 and a cylindrical barrel portion 921. The cylindrical portion 912 is configured to receive the barrel portion 921 so that the barrel portion 921 is rotatable within the cylindrical portion 912. In some embodiments, the cylindrical portion 912 may include two or more sections of the cylindrical wall 912A coupled together. In such embodiments, assembly of the adapter 150 may include placing the barrel portion 921 between sections of the cylindrical wall 912A and then coupling the sections of the cylindrical wall 912A together. In such embodiments, the sections of the cylindrical wall 912A may be screwed, bonded, or snapped together.

Figure 9B:
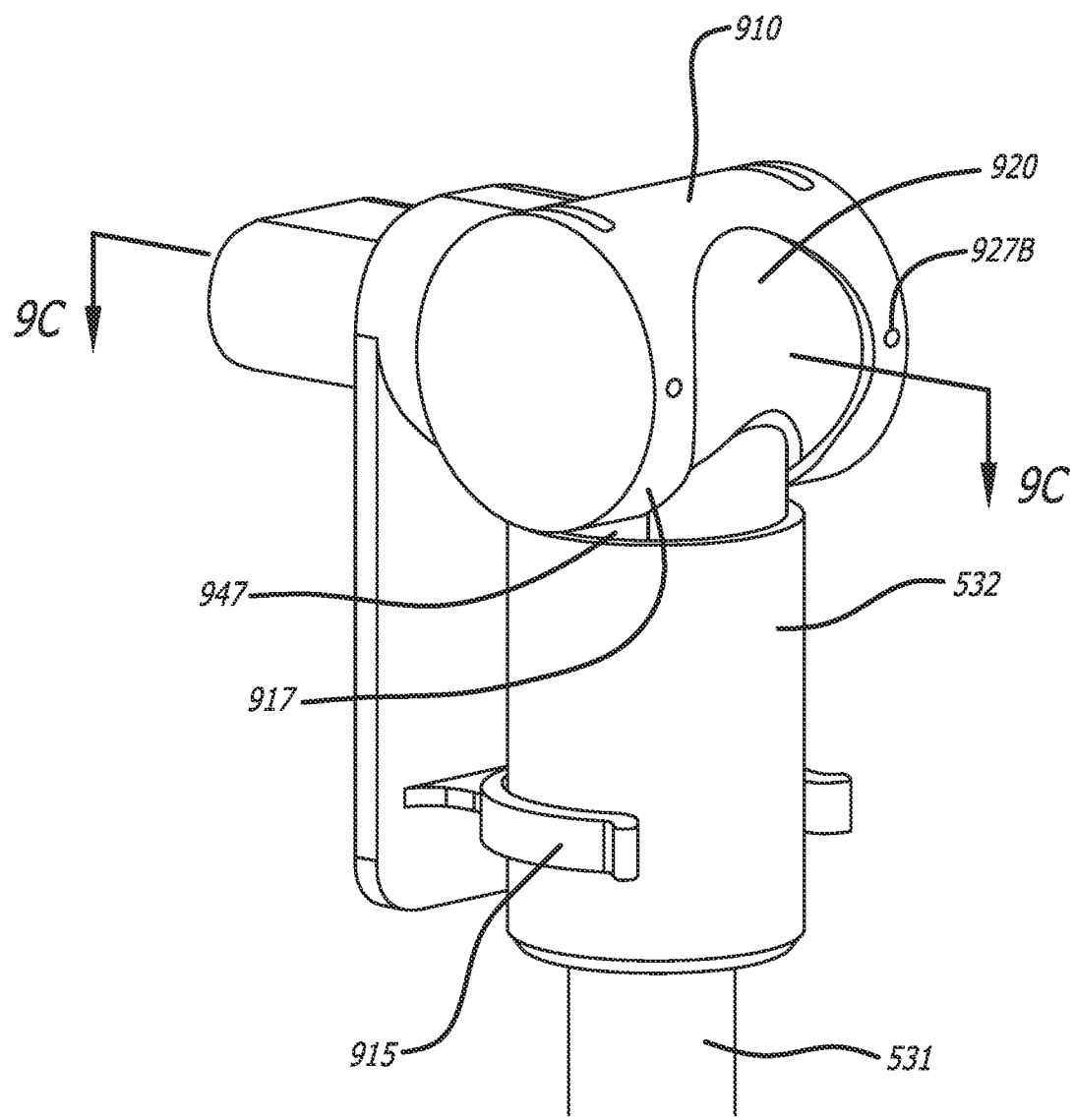
FIG. 9B illustrates the module-to-FDL connection adapter of FIG. 9A coupled to the FDL, in accordance with some embodiments.

The cylindrical portion 912 includes a slot 913 extending through a cylindrical wall 912A. The adapter connector 932 extends laterally away from the barrel portion 921 in a perpendicular direction with respect to the barrel portion 921. A width of the slot 913 is sized to facilitate disposition of the adapter connector 932 therethrough. The slot 913 extends along a circumference of the cylindrical portion 912 defining a length of the slot 913 sufficient to accommodate rotation of the barrel portion 921 across an angle of about 90 degrees while the adapter connector 932 is disposed through the slot 913. The slot 913 is positioned on the cylindrical portion 912 so that the barrel portion 921 may rotate from a first angular position to a second angular position. In the first angular position, the adapter connector 932 is disposed in a substantially horizontal orientation as depicted in FIG. 9A. In the second angular position, the adapter connector 932 is disposed in a substitutionally downward vertical orientation as depicted in FIG. 9B which illustrates the assembled adapter 150 coupled to the proximal FDL connector 532 with the barrel portion 921 disposed in the second angular position.

With further reference to FIG. 9A, the adapter 150 may include a retaining ring 926. The ring 926 is disposed within a recess 916 so that the ring 926 is sandwiched between the barrel portion 921 and the cylindrical wall 912A when the barrel portion 921 is received within the cylindrical portion 912 and so that the ring 926 co-rotates with the barrel portion 921. The ring 926 may be formed of a material having spring-like properties such as a spring steel, for example. The ring 926 may be formed so that the ring 926 defines friction force between the barrel portion 921 and the cylindrical portion 912 to inhibit rotation of the barrel 921 with respect to the cylindrical portion 912 in the absence of a deliberate rotational force applied by the clinician. The ring 926 may also include dimples or pins 927A configured to engage holes 927B in the cylindrical wall 912A when the barrel portion 921 is disposed in the first angular position, which engagement may provide a rotational detent to further prevent rotation of the barrel portion 921 away from the first angular position in the of a deliberate rotational force applied by the clinician.

The adapter 150 may be configured to provide a visual indication to the clinician as to the angular position of the barrel portion 921 with respect to the cylindrical portion 912. The barrel portion 921 may include one or more visual markers 923A shaped and positioned to be viewed through one or more corresponding visual openings 923B through the cylindrical wall 912A. In some embodiments, the visual markers 923A may include colored portions. For example, the visual markers 923A may include a first-colored portion (e.g., red) visible through the visual opening 923B when the barrel portion 921 is disposed in the first angular position, and the visual markers 923A may include a second-colored portion (e.g., green) visible through the visual opening 923B when the barrel portion 921 is disposed in the second angular position.

The adapter 150 may include a latching mechanism to secure the proximal FDL connector 532 to the adapter connector 932. The latching mechanism may include corresponding features of the proximal FDL connector 532 and the adapter 150. In an exemplary illustrated embodiment, the cylindrical wall 912A may include extending wall portions 917 protruding into the slot 913, and the proximal FDL connector 532 may include corresponding grooves 947 sized and positioned to receive the extending wall portions 917. The extending wall portions 917 are positioned to engage the grooves 947 when the barrel portion 921 is disposed in the second angular position, thereby preventing separation of the proximal FDL connector 532 from the adapter connector 932 when the barrel portion 921 is disposed in the second angular position.

In some embodiments, the extending wall portions 917 may be disposed in a plane (not shown) tangent to the cylindrical wall 912A and the grooves 947 may be an annular groove extending around the proximal FDL connector 532. In such an embodiment, the extending wall portions 917 may engage the grooves 947 at any angular orientation of the proximal FDL connector 532 about its longitudinal axis.

With reference to FIGS. 9A and 9B, the adapter 150 may include a securement mechanism 915. The securement mechanism 915 is configured to retain the barrel portion 921 in the second angular position when the proximal FDL connector 532 is coupled with the adapter connector 932. As shown in FIG. 9B, the securement mechanism 915 may include a clip that deflects and extends partially around the proximal FDL connector 532 to the constrain the proximal FDL connector 532 in the second angular position in the absence of a rotational force applied by the clinician urging the rotatable member 920 away from the second angular position. In other embodiments, the securement mechanism 915 may be configured so that the proximal FDL connector 532 is constrained in the vertically downward orientation in the absence of a non-rotational deliberate action by the clinician, i.e., a deliberate action that is independent from rotating the rotatable member 920, such as pressing a button or actuating a lever (not shown). In some embodiments, the adapter 150 may include a rotational biasing member (not show) such as a torsional spring, that is configured to rotationally urge the rotatable member 920 toward the first angular position.

In use, prior to connecting the FDL 130 to the TTM module 110, the barrel portion 921 may be disposed in first angular position so that the adapter connector 932 extends horizontally away from the TTM module 110. The clinician may then connect the proximal FDL connector 532 to the adapter connect 932. Thereafter, the clinician may grasp the proximal FDL connector 532 or a proximal portion of the FDL 130 and rotate the barrel portion 921 to the second angular position to activate the latching mechanism and secure the proximal FDL connector 532 within the clip 915. At the conclusion of the TTM therapy, the clinician may rotate the barrel portion 921 to the first angular position to deactivate the latching mechanism and disconnect the proximal FDL connector 532 from the adapter connect 932.

With reference to the FIG. 9A and FIG. 2, the adapter 150 may include a delivery valve 251 in line with the delivery lumen 903 and a return valve 252 in line with the return lumen 904. In the illustrated embodiment, the valves 251, 252 are controllable electro-mechanical valves. In other embodiments, the valves 251, 252 may be operated in accordance with rotation of the barrel portion 921. For example, one or both valves 251, 252 may be closed when the barrel portion 921 is disposed in the first angular position and then opened when the barrel portion 921 is rotated to the second angular position. In still other embodiments, the valves 251, 252 may be incorporated into the adapter connector 932 such as the valves illustrated in the first delivery valve 731 and the first return valve 732 of FIG. 7A. The adapter 150 may include an electrical connector 919 coupled to the adapter console 350 via a wire 919A. The electrical connector 919 is coupled with the console 300 when the adapter 150 is attached to the TTM module 110 so that the console 300 may supply electrical power to the adapter console 350.

Figure 9C:
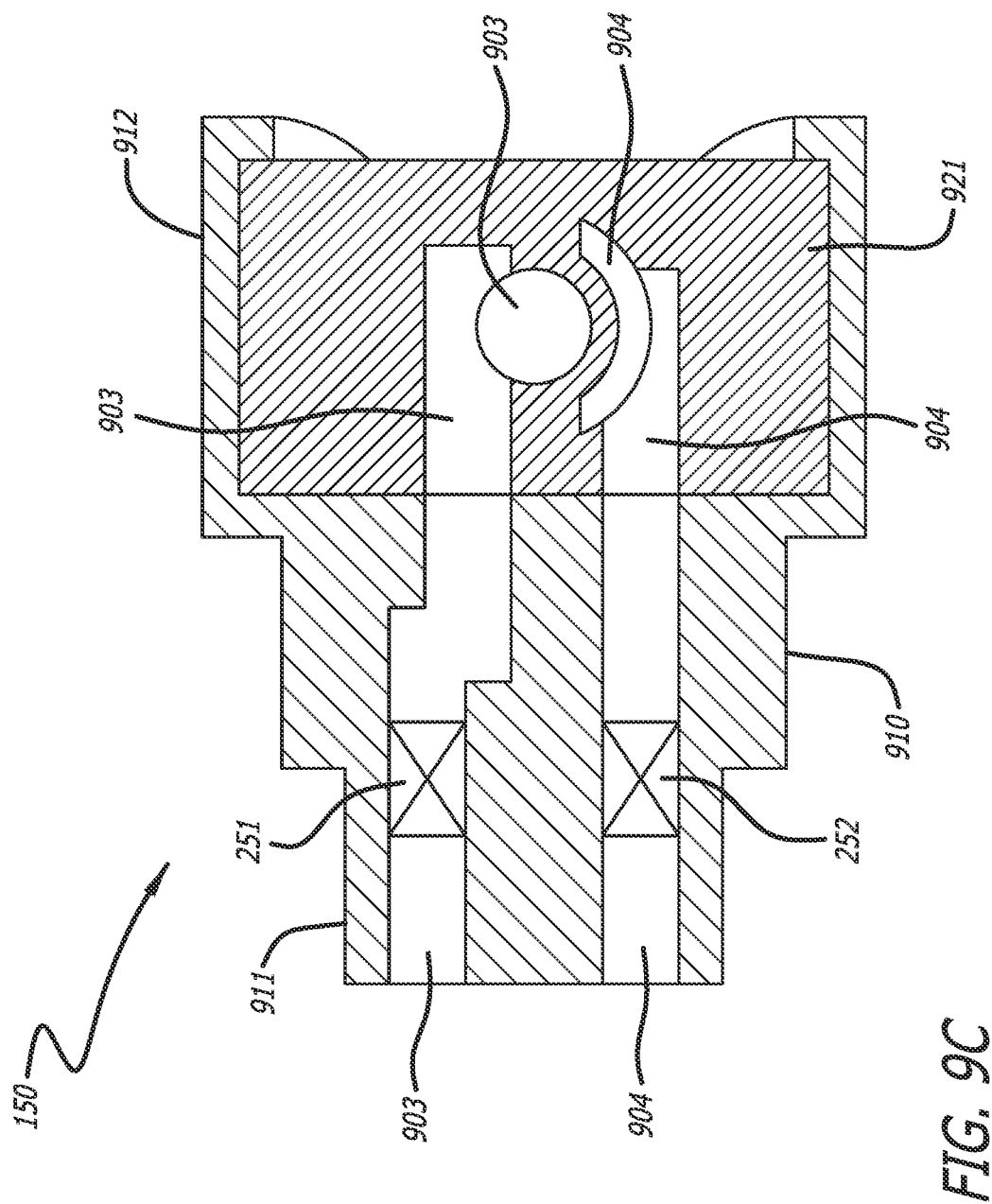
FIG. 9C shows a cross-sectional top view of the adapter of FIG. 9B cut along sectioning lines 9C-9C, in accordance with some embodiments.

FIG. 9C shows a cross-sectional top view of the adapter 150 cut along sectioning lines 9C-9C of FIG. 9B. As shown, the fluid delivery lumen 903 and the fluid return lumen 904 extend in a side-by-side arrangement through the input connector 911 and the housing 910 to the barrel portion 921. In the illustrated embodiment, the fluid delivery lumen 903 and the fluid return lumen 904 are converted from the side-by-side arrangement to a concentric arrangement within the barrel portion 921. In other embodiments, the fluid delivery lumen 903 and the fluid return lumen 904 may be converted from the side-by-side arrangement to a concentric arrangement within the housing 910. Also shown in FIG. 9C are the delivery valve 251 in line with the delivery lumen 903 and the return valve 252 in line with the fluid return lumen 904.

Figure 9D:
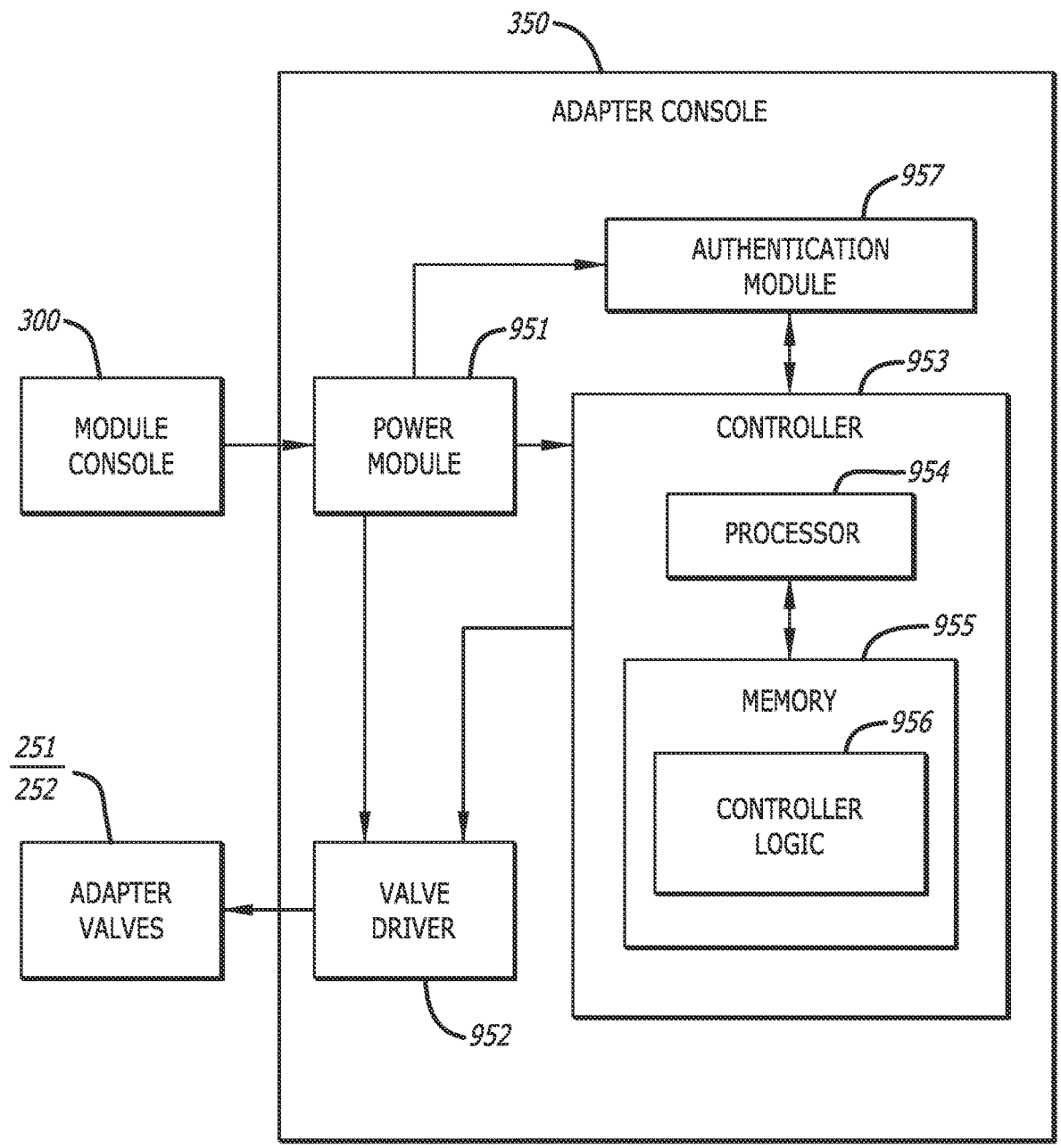
FIG. 9D illustrates a block diagram depicting various elements of a console of the module-to-FDL connection adapter, in accordance with some embodiments.

FIG. 9D illustrates a block diagram depicting various elements of the adapter console 350 including a power module 951, a valve driver 952, a controller 953, and an authentication module 957. The power module 951 receives from the TTM module console 300 and provides power to the other elements of the adapter console 350. The valve driver 952 is configured to activate the valves 251, 252 either individually or together in accordance with the controller logic 956. In the illustrated embodiment, the adapter console 350 may not be in signal communication with the console 300 of the TTM module 110.

The authentication module 957 is configured receive or otherwise obtain authentication data from an authentication tag. In some embodiments, the authentication module 957 may be a RFID reader. The authentication module 957 provides authentication data obtained from one or more authentication tags, such as the FDL authentication tag 557, the hub authentication tag 547, or the pad authentication tag 447, to the controller logic 956 of the controller 953 so that the processor 954 may perform various operations in accordance with the controller logic 956.

In some embodiments, the authentication information may include manufacturing information such as a manufacturing date range or a lot number. In some embodiments, any of the authentication tags 457, 547, 557 may provide data in a wired or wireless fashion. For example, the any of the authentication tags 457, 547, 557 may be a radio frequency identification (RFID) tag. In other embodiments, any of the authentication tags may refer to circuitry, where the circuitry provides authentication information via a wireless manner (e.g., via a wireless transmitter) or a wired manner such as via a data cable. In some embodiments, the adapter 150 may obtain power from the console, which in turn provides power to any of the authentication tags. For instance, power may be provided to the authentication tags 457, 557 via wiring 535 in the connector 532, coupled to the FDL conduit 531 and in the connector 533. Thus, upon the establishment of connections between the adapter 150, the FDL 130 and a connector including an authentication tag, the authentication tag receives power and, in response, transmits authentication back to the adapter 150 either via a wireless transmitter included within the circuitry or via the wiring 535 from which power was received. In one embodiment, a form of authenticated encryption and associated data (AEAD) using challenge-response techniques may be utilized in exchanging data between the adapter 150 and an authentication tag 447, 547, 557.

In some embodiments, the controller logic 956 may be configured to compare authentication data obtained from any or all of the authentication tags 447, 547, 557 with authentication information stored in memory 955 including a non-transitory, computer-readable medium. For example, the controller logic 956 may compare FDL identification data obtained from the FDL authentication tag 557 with approved FDL identification information stored in memory 955. As a result of the comparison, controller logic 956 may prevent the opening of one or both valves 251, 252 if the FDL identification data obtained from the FDL authentication tag 557 does not align with the approved FDL identification information stored in memory 955. As such, in the illustrated embodiment, the adapter 150 may enable or disable the circulation of TTM fluid 112 between the TTM module 110 and the pad set 120 independent of the flow control logic 343 of the console 300.

In other embodiments, the console 300 of the TTM module 110 may be in signal communication with the adapter console 350. In such embodiments, one or more of the patient therapy logic 341, the fluid temperature control logic 342 and/or the fluid flow control logic 343 may cause the processor 310 to perform one or more operations in accordance with authentication data obtained by the authentication module 957 from one or more authentication tags attached to the FDL 130, the hub 140 or any thermal pad of the pad set 120.

In some embodiments, the authentication tags 447, 547, or 557 may be configured to receive and store information such as therapy information. Such therapy information may include date, time, therapy duration, number of connections, number of thermal pads, TTM temperature, TTM flow rate and any other therapy or use information as may be contemplated by one of ordinary skill. In such embodiments, the operation of the TTM module 110 may be altered in accordance with information (e.g., the therapy information described above) stored in memory of one or more of the authentication tags 447, 547, or 557.

FIGS. 10A-10C illustrate a manifold hub 1040 having a plurality of distal hub connectors 1041 disposed in a line parallel to the longitudinal axis of the hub 1040. In some embodiments, the hub 1040 may include one or more distal hub connectors 1041. The distal hub connectors 1041 are configured to connect to fluid conduit connectors 471 of a pad set 120 (FIG. 1B). It is noted that the fluid conduit connectors 471 may vary is shape as seen in FIGS. 4A, 10A and 11A for instance. The hub 1040 also includes a proximal hub connector 1043 configured to connect to a distal FDL connector 533 of the FDL 130 (FIG. 5A). The hub 1040 may include an attachment member 1045 attached to the hub 1040 on a back side thereof. The attachment member 1045 may include one or more patches of a hook and loop fastener generally referred to as Velcro. As shown in FIG. 10B, the hub 1040 may be attached to an external apparatus such as a bed, a bed rail, or the like.

As shown in FIG. 10C, the attachment member 1045 may be attached to a thermal pad of the pad set 120. For example, a corresponding part of the hook and loop fastener may be attached to the thermal pad so that the hub 1045 may be attached to the thermal pad.

FIGS. 11A-11E illustrate a hub 1140 having a plurality of distal hub connectors 1141 disposed along a perimeter of the hub 1140. As shown in FIG. 11A, the hub 1140 may include up to six or more distal hub connectors 1141. The distal hub connectors 1141 are configured to connect to fluid conduit connectors 471 of a pad set 120. The hub 1140 also includes a proximal hub connector 1143 configured to connect to a distal FDL connector 533 of the FDL 130 (FIG. 5A).

The hub 1140 may include an attachment member 1145 attached to the hub 1140 on a back side thereof. The attachment member 1145 may include one or more patches of a first part of a hook and loop fastener generally referred to as Velcro. As shown in FIG. 11B, hub 1140 may be placed on a surface of the bed 60 so that the attachment member 1145 is coupled with the bed surface.

As shown in FIG. 11C, one or more thermal pads of the pad set 120 may include a portion such as a band 1143 having the corresponding second part of the hook and loop fastener 1146 attached thereto. In use, the clinician may couple the hub 1140 to the thermal pad via the corresponding fasteners 1145, 1146.

FIG. 11D illustrates the hub 1140 including an add-on clip 1142. As shown in FIG. 11E, the clip 1142 may be configured for attachment to an external apparatus such as a bedrail 61. In some embodiments, the clip 1142 may be removable from the hub 1140.

Figure 12:
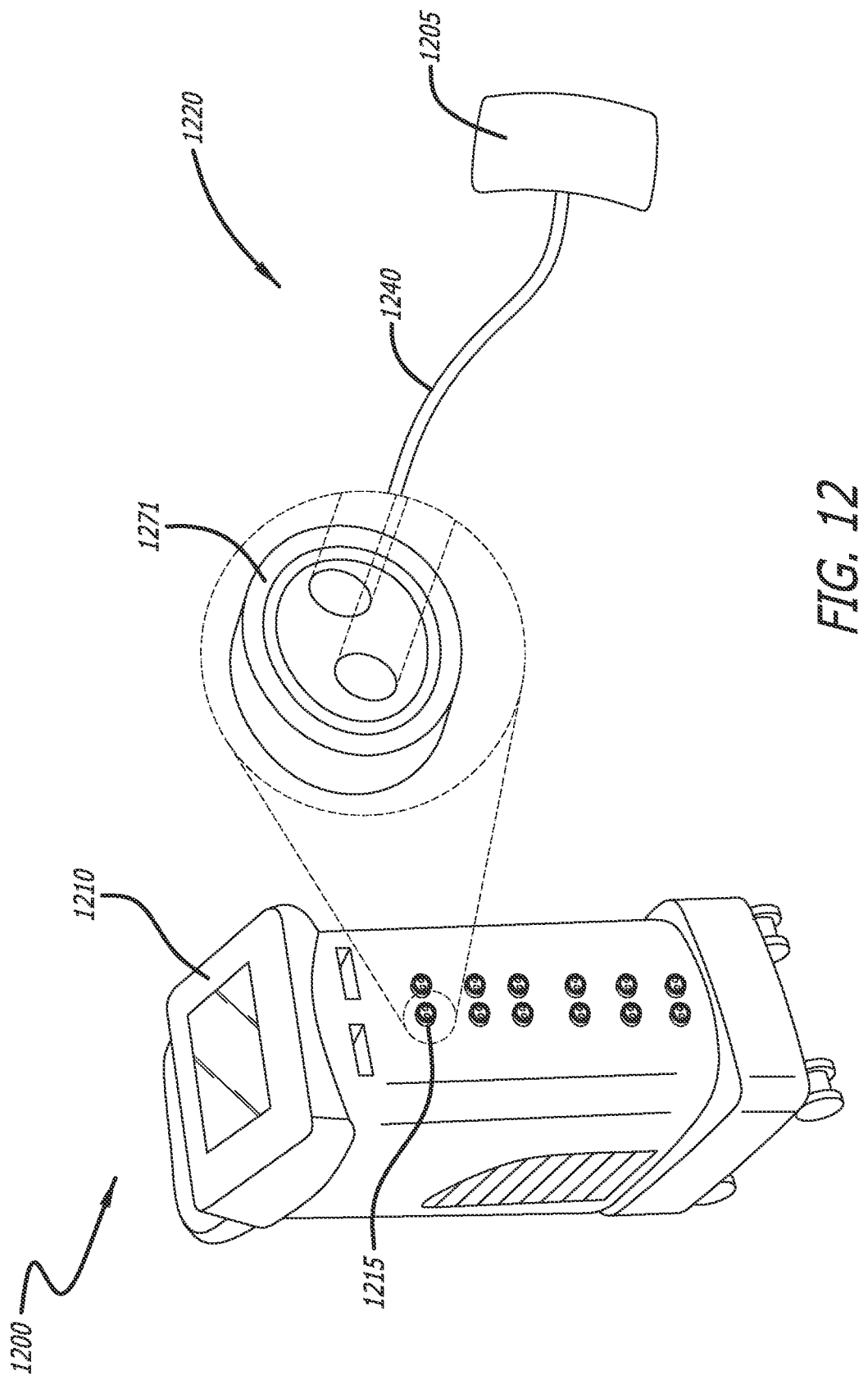
FIG. 12 illustrates another embodiment of a targeted temperature management (TTM) system, in accordance with some embodiments.

FIG. 12 illustrates a targeted temperature management (TTM) system 1200 including a TTM module 1210 and a pad set 1220. The TTM module 1210 includes a connection panel 1216 having a plurality of bi-liminal module connectors 1215. Each thermal pad of the pad set 1220 includes a bi-liminal fluid conduit 1240 extending continuously from the pad portion 1205 to the TTM module 1210. The fluid conduit 1240 includes a bi-liminal fluid conduit connector 1271 at a proximal end. The fluid conduit connector 1271 is configured to couple with the module connectors 1215. In some embodiments, the pad set 1220 may include up to six or more thermal pads and the connection panel 1216 may correspondingly include up to six or more module connectors 1215. Any and all portions of the bi-luminal connection system 700 may be employed with the TTM system 1200 to define a fluid connection between any two fluid connection entities, such as between any module connector 1215 and any fluid conduit connector 1271.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A fluid delivery line (FDL) for use in transporting a targeted temperature management (TTM) fluid between a TTM module and a thermal contact pad applied to a patient, the FDL comprising:
 a bi-luminal fluid conduit extending from a proximal end to a distal end;
 a bi-luminal proximal FDL connector at the proximal end, wherein:
  the proximal FDL connector is configured to couple with the TTM module, and
  the two lumens of the proximal FDL connector are concentrically arranged; and
 a bi-luminal distal connector at the distal end configured to couple with a manifold hub, the bi-luminal distal connector comprising a pair of valves, each valve disposed in line with a separate one of the two lumens, and wherein each valve is configured to automatically:
  prevent fluid flow through its respective lumen when decoupled with the distal connector from the manifold hub, and
  permit fluid flow through its respective lumen when coupled with the distal connector with the manifold hub.

2. The fluid delivery line of claim 1, wherein the distal connector comprises a latching mechanism including a displaceable member, wherein when the displaceable member is in a displaced state, detachment of the distal connector from the manifold hub is permitted, and when the displaceable member is in a non-displaced state, detachment of the distal connector from the manifold hub is prevented.

3. The fluid delivery line of claim 1, wherein the two lumens of the distal connector are concentrically arranged.

4. The fluid delivery line of claim 1, wherein, when coupling to the distal connector, the proximal FDL connector is configured to:
connect to a module connector of the TTM module, and
pivot from a first position to a second position, wherein the first position is such that a longitudinal axis is situated in a substantially horizontal orientation, and the second position is such that the longitudinal axis is situated in a substantially vertical orientation.

5. The fluid delivery line of claim 4, wherein the proximal FDL connector is configured to latch to the TTM module, wherein when the proximal FDL connector is oriented:
horizontally, a latching mechanism is deactivated and separation of the proximal FDL connector from an adapter is allowed, and
vertically, the latching mechanism is activated and separation of the proximal FDL connector from the adapter is prevented.

6. The fluid delivery line of claim 1, wherein the proximal FDL connector comprises a pair of proximal valves, each proximal valve disposed in line with a separate one of the two lumens of the proximal FDL connector, and wherein each proximal valve is configured to automatically:
prevent fluid flow through its respective lumen upon decoupling of the proximal FDL connector from the TTM module, and
permit fluid flow through its respective lumen upon coupling of the proximal FDL connector with the TTM module.

7. The fluid delivery line of claim 1, further comprising an authentication tag configured to provide FDL authentication data to the TTM module.

8. The fluid delivery line of claim 1, wherein the FDL is coupled with the manifold hub, the manifold hub comprising a plurality of bi-luminal distal hub connectors configured to couple with a plurality of thermal contact pads.

9. The fluid delivery line of claim 1, wherein the FDL is coupled with more than one manifold hub, each manifold hub comprising a plurality of bi-luminal distal hub connectors configured to couple with a plurality of thermal contact pads.

10. The fluid delivery line of claim 1, wherein the two lumens of the fluid conduit are concentrically arranged along at least portion of the fluid conduit.

11. A thermal contact pad assembly for exchanging thermal energy between a targeted temperature management (TTM) fluid and a patient, the assembly comprising:
a thermal contact pad comprising:
a pad portion configured for placement on the patient;
a bi-luminal fluid conduit extending proximally away from the pad portion; and
a bi-luminal pad connector coupled to the fluid conduit at a proximal end; and
a manifold hub comprising:
a housing;
a bi-luminal distal hub connector coupled with the bi-luminal pad connector; and
a bi-luminal proximal hub connector configured to couple with a bi-luminal fluid delivery line (FDL) of a TTM system,
wherein the TTM fluid flows through the housing between flowing through the bi-luminal distal hub connector and the bi-luminal proximal hub connector, and
wherein the bi-luminal proximal hub connector includes two lumens that are disposed in a concentric arrangement.

12. The assembly of claim 11, wherein the bi-luminal proximal hub connector comprises a pair of valves, each valve disposed in line with a separate one of the two lumens, and
wherein each valve is configured to automatically:
prevent fluid flow through its respective lumen upon decoupling of the bi-luminal proximal hub connector from the FDL, and
permit fluid flow through its respective lumen upon coupling of the bi-luminal proximal hub connector with the FDL.

13. The assembly of claim 11, wherein the bi-luminal proximal hub connector is configured to couple with the FDL via a proximal latching mechanism, the proximal latching member including a displaceable member, such that when the displaceable member is in:
a displaced state, detachment of the bi-luminal proximal hub connector from the FDL is allowed, and
a non-displaced state, detachment of the bi-luminal proximal hub connector from the FDL is prevented.

14. The assembly of claim 11, wherein
each bi-luminal distal hub connector in combination with a corresponding pad connector comprises a distal latching mechanism, and
at least one of the bi-luminal distal hub connector or pad connector includes a displaceable member of the distal latching mechanism such that when the displaceable member of the distal latching mechanism is in:
a displaced state, detachment of the pad connector from the bi-luminal distal hub connector is allowed, and
a non-displaced state, detachment of the pad connector from the bi-luminal distal hub connector is prevented.

15. The assembly of claim 11, wherein the manifold hub comprises a plurality of the bi-luminal distal hub connectors, each bi-luminal distal hub connector configured to couple with a pad connector, wherein:
each bi-luminal distal hub connector includes a pair of valves,
each valve of the pair of valves is disposed in line with a separate one of the two lumens, and
each valve of the pair of valves is configured to automatically:
prevent fluid flow through its respective lumen upon decoupling of the distal hub connector from the pad connector, and
permit fluid flow through its respective lumen upon coupling of the distal hub connector with the pad connector.

16. The assembly of claim 11, wherein the two lumens of the bi-luminal distal hub connector are concentrically arranged.

17. The assembly of claim 11, further comprising a plurality of thermal contact pads coupled with the manifold hub via a plurality of the bi-luminal distal hub connectors.

18. The assembly of claim 11, further comprising an authentication tag attached to at least one of the thermal contact pad or the manifold hub, the authentication tag configured to provide authenticating data to a TTM module of the TTM system.

19. The assembly of claim 11, wherein the manifold hub comprises an attachment device configured to couple the manifold hub with at least one of the thermal contract pad, a bed surface, or a bedrail.

20. A targeted temperature management (TTM) system comprising:
- a TTM module configured to provide a TTM fluid;
- a thermal pad configured to facilitate thermal energy transfer between the TTM fluid and a patient, the thermal pad comprising:
  - a pad portion configured for placement on the patient; and
  - a bi-luminal fluid conduit extending proximally away from the pad portion;
- a bi-luminal fluid delivery line (FDL) configured for transporting TTM fluid between the TTM module and the thermal pad, the bi-luminal FDL including a proximal bi-luminal FDL connector at a proximal end of the bi-luminal FDL and a distal bi-luminal FDL connector at a distal end of the bi-luminal FDL; and
- a manifold hub coupled to the bi-luminal FDL at the distal end of the bi-luminal FDL, the manifold hub configured to facilitate a bi-luminal fluid connection between the bi-luminal FDL and the bi-luminal fluid conduit, wherein coupling the bi-luminal FDL to the TTM module comprises:
  - coupling the proximal bi-luminal FDL connector of the FDL to a bi-luminal module connector of the TTM module, wherein the proximal bi-luminal FDL connector includes two lumens that are concentrically arranged; and
  - opening a pair of valves of the TTM module, each valve disposed in line with a separate one of the two lumens of the bi-luminal module connector, to allow bi-directional flow of the TTM fluid through the bi-luminal module connector.

21. The system of claim 20, further comprising a connection adapter attached to the TTM module, wherein the connection adapter comprises the pair of valves and the bi-luminal module connector.

22. The system of claim 21, wherein the connection adapter comprises an adapter console including a controller having a processor and controller logic stored in memory, and wherein the controller logic is configured to selectively open and close the pair of valves.

23. The system of claim 22, wherein the adapter console comprises an authentication module configured to obtain authentication data from an authentication tag attached to at least one of the FDL, the manifold hub or the thermal pad.

24. The system of claim 23, wherein the controller logic is configured to open the pair of valves when the obtained authentication data aligns with authentication information stored in memory.

25. The system of claim 21, wherein the connection adapter comprises a latching mechanism configured to secure the proximal FDL connector to the connection adapter.

26. The system of claim 25, wherein the latching mechanism comprises a pivoting member coupled with the proximal FDL connector so that the proximal FDL connector is rotatable between a horizontal orientation and a vertical orientation, such that when the proximal FDL connector is oriented:
- horizontally, the latching mechanism is deactivated and separation of the proximal FDL connector from the connection adapter is allowed, and
- vertically, the latching mechanism is activated and separation of the proximal FDL connector from the connection adapter is prevented.

27. The system of claim 26, wherein the latching mechanism includes a clip configured to engage the proximal FDL connector and thereby constrain the proximal FDL connector in the vertical orientation.

28. The system of claim 20, wherein the manifold hub is coupled to the FDL via a bi-luminal proximal hub connector comprising a pair of hub valves, each hub valve disposed in line with a separate one of the two lumens of the proximal hub connector, and
wherein each hub valve is configured to automatically:
- prevent fluid flow through its respective lumen upon decoupling of the proximal hub connector from the FDL, and
- permit fluid flow through its respective lumen upon coupling of the proximal hub connector with the FDL.

29. The system of claim 20, wherein the proximal hub connector is configured to couple with the FDL via a proximal latching mechanism, the proximal latching including a displaceable member, such that when the displaceable member is in:
- a displaced state, detachment of the proximal hub connector from the FDL is allowed, and
- a non-displaced state, detachment of the proximal hub connector from the FDL is prevented.

* * * * *